US010642942B2

(12) United States Patent
Bressloff

(10) Patent No.: US 10,642,942 B2
(45) Date of Patent: May 5, 2020

(54) METHOD OF MAPPING IMAGES OF HUMAN DISEASE AND OF DESIGNING OR SELECTING A MEDICAL DEVICE USING A SURROGATE MODEL

(71) Applicant: University of Southampton, Southampton (GB)

(72) Inventor: Neil W. Bressloff, Southampton (GB)

(73) Assignee: Neil W. Bressloff, Southampton (GB)

( * ) Notice: Subject to any disclaimer, the term of this patent is extended or adjusted under 35 U.S.C. 154(b) by 638 days.

(21) Appl. No.: 15/118,526

(22) PCT Filed: Feb. 13, 2015

(86) PCT No.: PCT/GB2015/050419
§ 371 (c)(1),
(2) Date: Aug. 12, 2016

(87) PCT Pub. No.: WO2015/121674
PCT Pub. Date: Aug. 20, 2015

(65) Prior Publication Data
US 2017/0076014 A1    Mar. 16, 2017

(30) Foreign Application Priority Data

Feb. 14, 2014 (GB) .................................. 1402643.9

(51) Int. Cl.
*A61B 6/00* (2006.01)
*G06F 17/50* (2006.01)
(Continued)

(52) U.S. Cl.
CPC .............. *G06F 17/50* (2013.01); *A61B 6/504* (2013.01); *A61B 6/5211* (2013.01);
(Continued)

(58) Field of Classification Search
CPC .............................. A61B 6/503; Y10S 623/90
See application file for complete search history.

(56) References Cited

U.S. PATENT DOCUMENTS 7,529,431 B2    5/2009 Bayer et al.
2002/0068968 A1    6/2002 Hupp
(Continued)

FOREIGN PATENT DOCUMENTS

EP    1177779 A2    2/2002
EP    2710978 A1    3/2014
(Continued)

OTHER PUBLICATIONS

"International Application No. PCT/GB2015/050419, International Search Report dated Apr. 30, 2015", (dated Apr. 30, 2015), 4 pgs.
(Continued)

*Primary Examiner* — Omkar A Deodhar
(74) *Attorney, Agent, or Firm* — Schwegman Lundberg & Woessner, P.A.

(57) ABSTRACT

A method of designing or selecting an implantable medical device comprises the steps of: i) obtaining a plurality of measured data points of a characteristic of an anatomical feature of an individual; ii) using said data points to construct a surrogate model of said characteristic, the surrogate model being constructed by interpolating or regressing measured data points of the characteristic, and using said surrogate model to obtain predicted values of said characteristic at a plurality of locations; iii) using said predicted values to determine or select at least one value of a design parameter of the implantable medical device. There is further disclosed a method of monitoring or diagnosing a disease or disorder.

15 Claims, 20 Drawing Sheets

(51) Int. Cl.
*A61B 8/12* (2006.01)
*A61B 8/08* (2006.01)
*G16H 50/50* (2018.01)
*A61F 2/915* (2013.01)
*A61B 34/10* (2016.01)
*G06F 19/00* (2018.01)
*G06F 17/11* (2006.01)
*A61B 17/00* (2006.01)

(52) U.S. Cl.
CPC .............. *A61B 8/0891* (2013.01); *A61B 8/12* (2013.01); *A61B 8/5215* (2013.01); *A61B 34/10* (2016.02); *A61F 2/915* (2013.01); *G06F 17/11* (2013.01); *G06F 19/00* (2013.01); *G16H 50/50* (2018.01); *A61B 8/483* (2013.01); *A61B 2017/00526* (2013.01); *A61F 2002/91533* (2013.01); *A61F 2002/91575* (2013.01); *A61F 2240/002* (2013.01); *A61F 2250/0018* (2013.01)

(56) References Cited

U.S. PATENT DOCUMENTS

| | | | |
|---|---|---|---|
| 2003/0200120 A1 | 10/2003 | Binkert | |
| 2005/0043609 A1* | 2/2005 | Murphy | G16H 50/50 600/408 |
| 2006/0058638 A1 | 3/2006 | Boese et al. | |
| 2006/0204069 A1* | 9/2006 | Le Bras | A61B 6/505 382/132 |
| 2007/0167763 A1 | 7/2007 | Hyun | |
| 2008/0009746 A1* | 1/2008 | Forster | A61B 5/0536 600/467 |
| 2008/0201007 A1* | 8/2008 | Boyden | A61F 2/06 700/119 |
| 2008/0298659 A1 | 12/2008 | Spence et al. | |
| 2013/0144573 A1 | 6/2013 | Sharma et al. | |
| 2013/0296998 A1 | 11/2013 | Leotta et al. | |

FOREIGN PATENT DOCUMENTS

| | | |
|---|---|---|
| KR | 10-2007-0059260 A | 6/2007 |
| WO | WO-9104544 A1 | 4/1991 |
| WO | WO-9824065 A1 | 6/1998 |
| WO | WO-02/15823 A1 | 2/2002 |
| WO | WO-02/29758 A2 | 4/2002 |
| WO | WO-02/064011 A2 | 8/2002 |
| WO | WO-2004/026178 A1 | 4/2004 |
| WO | WO-2007/149428 A1 | 12/2007 |
| WO | WO-2011/050234 A2 | 4/2011 |
| WO | WO-2014/053616 A1 | 4/2014 |

OTHER PUBLICATIONS

"International Application No. PCT/GB2015/050419, Written Opinion dated Apr. 30, 2015", (dated Apr. 30, 2015), 6 pgs.

"International Application No. PCT/GB2015/050419, International Preliminary Report on Patentability dated Aug. 25, 2016", 8 pgs.

"United Kingdom Application Serial No. GB1402643.9, Examination Opinion dated Aug. 27, 2014", 6 pgs.

Jones, Donald R., "A Taxonomy of Global Optimization Methods Based on Response Surfaces", *Journal of Global Optimization*, 21, (2001), 345-383.

Pant, Sanjay, et al., "Multiobjective design optimisation of coronary stents", *Biomaterials*, 32(31), (Nov. 2011), 1-24

* cited by examiner

Fig. 2d)
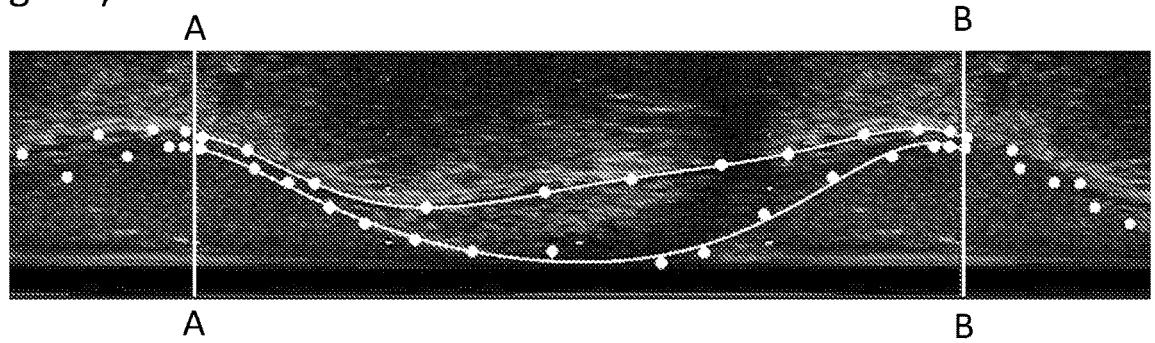
Fig. 2e)
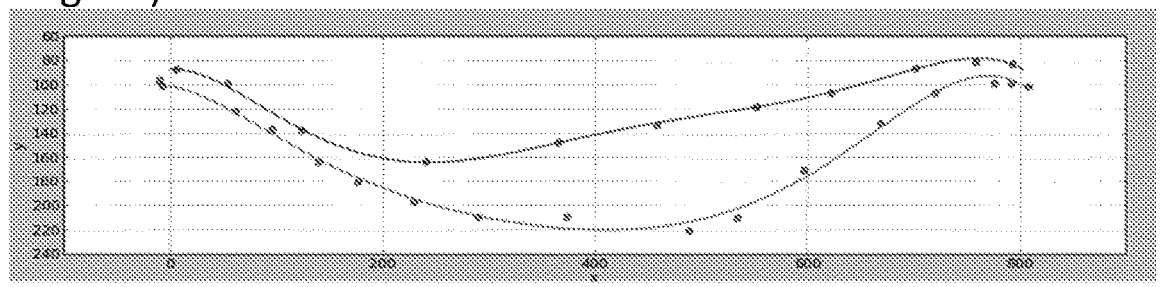
Fig. 2f)
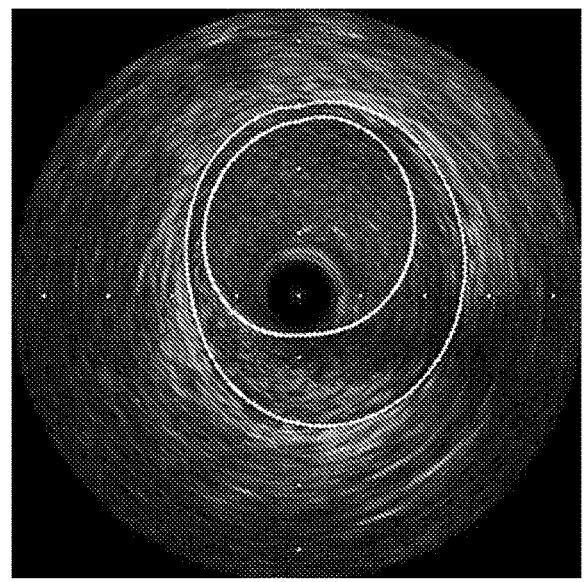
Fig. 2

Fig. 8b
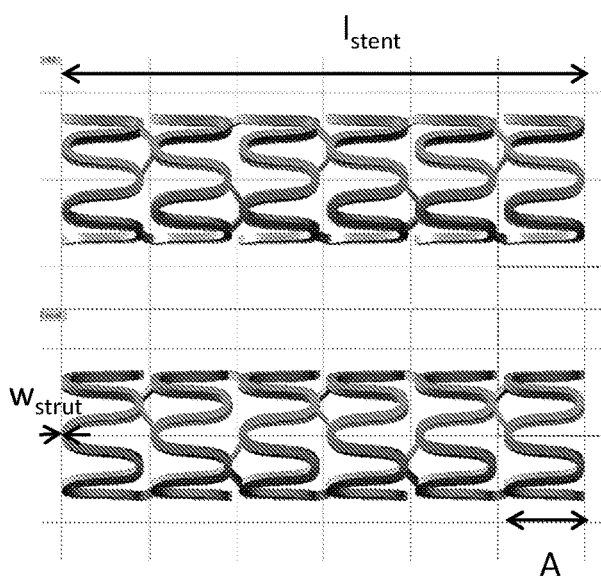
Fig. 8c
Fig. 8d
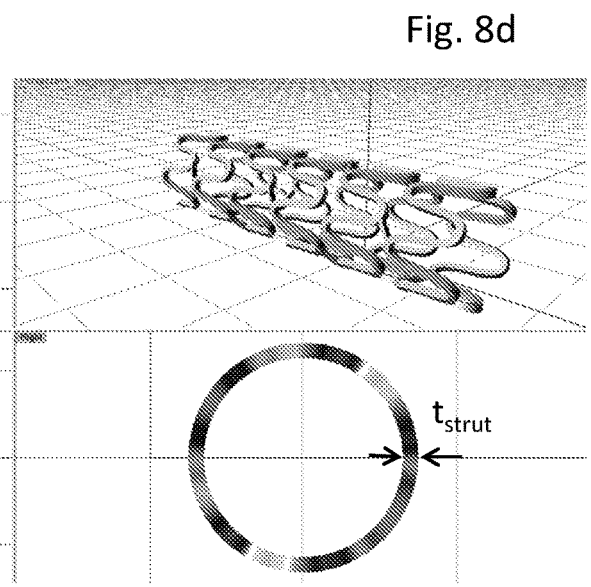
Fig. 8e (a)
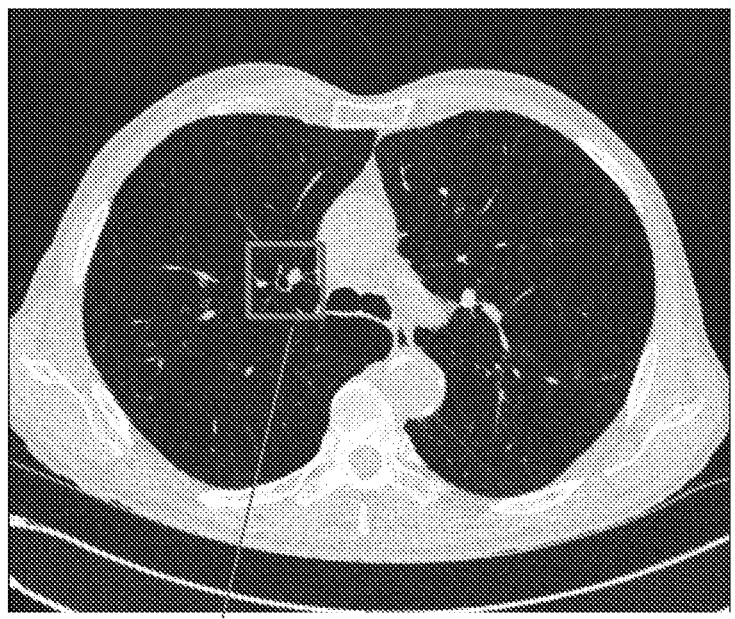
(b)
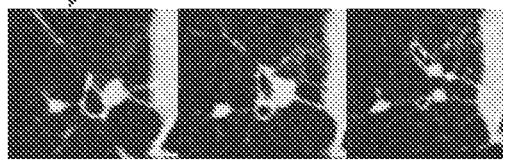
Fig. 18

METHOD OF MAPPING IMAGES OF HUMAN DISEASE AND OF DESIGNING OR SELECTING A MEDICAL DEVICE USING A SURROGATE MODEL

PRIORITY APPLICATIONS

This application is a U.S. National Stage Filing under 35 U.S.C. 371 from International Application No. PCT/GB2015/050419, filed on 13 Feb. 2015, and published as WO 2015/121674 on 20 Aug. 2015, which claims the benefit of priority to United Kingdom Application No. 1402643.9, filed on Feb. 14, 2014; which applications and publication are incorporated herein by reference in their entirety.

FIELD OF THE INVENTION

The present invention relates to implantable medical devices, methods of designing or selecting implantable medical devices, computer program products to execute methods of designing implantable medical devices, methods of manufacturing implantable medical devices and methods of monitoring or diagnosing diseases or disorders.

BACKGROUND

Implantable medical devices include devices such as stents, grafts, valves, filters and prosthetic implants such as hip implants used in hip replacement surgery. The devices are implanted into a patient and it is usually intended that they remain implanted in the patient permanently. The implanted device is often chosen from a standard range of available sizes and shapes based on patient specific anatomy.

A stent is a deformable tubular structure which can be inserted into a vessel or passage in the body of a patient. For example, when an artery has become narrowed or constricted, an arterial stent can be implanted in the diseased segment of the artery, in order to keep the artery open and recover normal blood flow.

For a particular patient, a stent will typically be selected from an available range. Various imaging techniques are used to diagnose the type and extent of a disease and select the most appropriate stent. For an arterial stent, the selection is based on the target vessel diameter and the distribution and extent of the disease, which can be determined using imaging techniques such as IVUS (intravascular ultrasound) and angiography. The stent is chosen such that it has a length and diameter suitable to be implanted within the artery, and such that it can be expanded to the appropriate diameter to keep the artery open.

There are several problems associated with this approach. The range of stents available for implantation may be limited to a small number of different stent designs. The suitability of the stent depends on the skill and experience of the interventionist who determines the distribution and extent of the disease and selects the stent. Further, the stents are standard, off-the-shelf, uniform designs and are known to produce sub optimal scaffolding in locations of challenging, irregular, non-homogenous disease. Failure rates of existing devices are measured in single digit percentages.

Currently, the selection of the best stent from the available range relies on the skill and experience of the interventionist. The interventionist must correctly identify the features, and determine the size of the lumen correctly. The interventionist does not take into account features such as the morphology of the disease when selecting the stent, although these features are important considerations. Incorrect selection of a stent which is not the optimal stent for a specific patient from the provided range can cause complications and even failure.

Failure or complications can also occur if a stent with the optimal configuration for the type and shape of the diseased tissue is not available. The size of the artery and the length of the diseased section vary from patient to patient. Furthermore, the plaques or lesions formed on the artery walls which cause the narrowing can be of varying size and shape. The plaques may also be formed of different types of diseased tissue. For example, parts of the diseased tissue may be softer material such as fatty or fibrous tissue, whereas in other areas calcification may occur. Calcified regions of the diseased tissue may be widespread. The degree of distribution of the calcification of the artery is a secondary consideration when selecting a stent.

The location of the diseased tissue may also present complications. For example, left main stem coronary bifurcation stents in particular have a relatively higher failure rate. This is most likely due to the differing diameters of the three vessels, and the variation in the angle between the branches. A further example of a location for which complications may occur is when a stent is implanted in order to exclude an aneurysm, where percutaneous covered stenting options are used. In this case, a stent of a standard off-the-shelf design may result in blocked side branches at the aneurysmal segment of the vessel, since the stents are covered in order to exclude the aneurysm itself. Complications arising from this include paralysis, renal impairment and mesenteric ischaemia.

International patent application number WO 2007/149428 relates to a stent customization system and method. This document includes a general description of the process of patient specific stent design and contains a general description of a process of customizing attributes of a stent based on measurements relating to a specific patient. The document describes using a measured value of a patient attribute such as vessel size to select and customize a template. However, it does not take into account the variation of the disease along the section of the artery in which the stent is to be located. The document does not disclose adjusting the design parameters of the stent at different locations along the stent according to the variation in disease characteristics.

WO 2004/026178 discloses taking MRI scans of an aorta, and using smoothing algorithms within CAD software to interpolate between successive MRI images to produce a CAD model. A physical model of the aorta is then produced and used in manufacturing processes to produce a stent. The model disclosed in WO 2004/026178 does not take into account the variation of the characteristic throughout the measured part of the anatomy.

US 2008/201007 discloses a method in which a three-dimensional solid model of the blood vessel sleeve is constructed by interpolating data that represents the blood vessel sleeve surface between curvature contours. The model disclosed in US 2008/201007 does not take into account the variation of the characteristic throughout the measured part of the anatomy.

The above has been explained specifically in relation to vascular stents; however, the present invention is not limited to such. The above described problems are also relevant to the selection and design of stents for use in other parts of the body, and to other implantable medical devices such as hip implants and heart valves. The present invention seeks to alleviate one or more of the above problems.

SUMMARY OF THE INVENTION

According to one aspect of the present invention, there is provided a method of designing or selecting an implantable medical device, comprising the steps of:
i) obtaining a plurality of measured data points of a characteristic of an anatomical feature of an individual;
ii) using said data points to construct a surrogate model of said characteristic, and using said surrogate model to obtain predicted values of said characteristic at a plurality of locations;
iii) using said predicted values to determine or select at least one value of a design parameter of the implantable medical device.

In one embodiment, the surrogate model is constructed by interpolating or regressing measured data points of the characteristic.

In one embodiment, the surrogate model is a response surface model.

In one embodiment, the response surface model or surrogate model provides a complete map, or predictor, of the characteristic in the region defined by the upper and lower bounds of the input data. In one embodiment, each of the predicted values at a plurality of locations are obtained by interpolating or regressing the same set of measured data points.

In one embodiment, step iii) comprises using said predicted values to determine values of the design parameter of the implantable medical device at locations on the device that correspond, when the device is implanted, to the locations of the predicted values.

In one embodiment, step iii) comprises using said predicted values to select a value of a design parameter of the implantable medical device from a range of values of the design parameter for which a device is available. In one embodiment, step iii) comprises using said predicted values to determine a value of a design parameter of the implantable medical device and selecting an implantable medical device from a range of existing implantable medical devices for which the design parameter is closest to the determined value.

In one embodiment, step i) comprises obtaining the plurality of measured data points from anatomical images. In one embodiment, the anatomical images are a plurality of intravascular ultrasound images, and in a further embodiment, the anatomical images are a plurality of intravascular ultrasound images of sections of an artery at locations along the diseased section of the artery. In another embodiment, the anatomical images are obtained using Magnetic Resonance Imaging. In one embodiment, the anatomical images are obtained using X-ray imaging. In another embodiment, the anatomical images are obtained using X-ray computed tomography. In another embodiment, the measured data points are obtained from X-ray angiography data. In another embodiment, the anatomical images are obtained using other intravascular imaging modalities such as optical coherence tomography (OCT).

In one embodiment, step i) comprises obtaining the measured data points at a plurality of locations circumferentially around the artery for each section of the artery. In one embodiment, step i) comprises transforming the image to a rectangular pixel grid, where the location of each pixel in the horizontal direction corresponds to the angular coordinate and the location in the vertical direction corresponds to the radial coordinate. In a further embodiment, step i) further comprises defining two sets of points on the image and fitting lines of best fit to each set of points, such that the difference between the lines of best fit can be measured at specific locations on the grid.

In one embodiment, the surrogate model is constructed using a least squares polynomial fit to the measured data points. In this embodiment, the surrogate model is constructed by minimizing the sum of squared residuals, the residuals being the difference between a measured data point and the predicted value provided by the model at the same location as the data point.

In one embodiment, each polynomial term in the polynomial fit is a basis function. A polynomial series is a linear combination of basis functions.

In one embodiment, the surrogate model is constructed using regression when the noise in the measured data points is greater than a pre-determined threshold value.

In one embodiment, the regression model can be constructed using Kriging. In this embodiment, the Kriging formulation of the surrogate model is adapted to regress by adding regression constants to the leading diagonal of the correlation matrix, R, as defined below.

In one embodiment, step ii) comprises interpolating the measured data points using a linear combination of basis functions. Each basis function corresponds to a measured data point. The basis functions are radial basis functions, each centred around one of the measured data points. A radial basis function is a function whose value depends only on the distance from the centre, in this case the location of the measured data point.

In one embodiment, the surrogate model comprises a response surface. In one embodiment, the response surface interpolates the measured data points using a linear combination of basis functions. A response surface is a mathematical fit to a set of input-output data points. The input data is the set of measured data points. The output data is the dependent response at each input data point, for example the $\hat{v}(z^*)$ described below. Various response surfaces may be constructed for various characteristics from the same input data.

In one embodiment, step ii) comprises constructing said surrogate model using the method of Kriging. Kriging is sometimes referred to as a form Bayesian Inference, or as a Gaussian Process. The predicted values of the characteristic, $\hat{v}(z^*)$, at locations $z^*$ are given by the equation:

$$\hat{v}(z^*) = \hat{\mu} + \sum_{i=1}^{n} b_i \varphi(z^* - z_i)$$

where $z^*$ is the location at which said predicted values are obtained, $z_i$ is a d-dimensional vector which is the location of a measured data point, $b_i$ is the ith element of $R^{-1}(v - 1\hat{\mu})$, $\varphi(z^* - z_i)$ is given by the equation $$\varphi(z^* - z_i) = \exp\left(-\sum_{l=1}^{d} \theta_l |z_l^* - z_{i,l}|^{p_l}\right)$$

and $\hat{\mu}$ is given by the equation $$\hat{\mu} = \frac{1'R^{-1}v}{1'R^{-1}1}$$

where 1 is an n×1 vector of ones $$1 = \begin{pmatrix} 1 \\ \vdots \\ 1 \end{pmatrix}, v = \begin{pmatrix} v_1 \\ \vdots \\ v_n \end{pmatrix}$$

is a vector of the values of the measured data points, R is an n×n matrix with each element (i, j) given by the function $\exp(-\Sigma_{l=1}^{d}\theta_l|z_{il}-z_{jl}|^{p_l})$, $p_l$ is an estimated parameter satisfying $0 < p_l \leq 2$ and $\theta_l$ is an estimated parameter satisfying $\theta_l \geq 0$.

In this embodiment, $\hat{v}(z^*)$ is a response surface model.

In one embodiment, the estimates for the values of $\theta_l$ are obtained by maximising the concentrated ln-likelihood function. In a further embodiment, an expected improvement calculation is used to determine further locations at which to obtain measured data points in order to improve the surrogate model.

In another embodiment, the surrogate model is constructed using basis functions. The surrogate model is constructed by interpolating the measured data points using a linear combination of polynomial terms and a linear combination of radial basis function terms. Each radial basis function term is centred around one of the measured data points, i.e. its value depends only on the distance from the centre, in this case the location of the measured data point.

The predicted values $\hat{v}(z^*)$ are given by the equation:

$$\hat{v}(z^*) = \sum_{k=1}^{m} a_k \pi_k(z^*) + \sum_{j=1}^{n} b_j \varphi(z^* - z_j)$$

where $z^*$ is the location at which said predicted values are obtained, $z_j$ is the location of a measured data point, $\varphi(z^*-z_j)$ is the basis function, $\pi_k(z)$ is a basis of the set of all polynomials in z of degree G and $a_k$ and $b_j$ are determined by solving the set of equations:

$$v_i = \sum_{k=1}^{m} a_k \pi_k(z_i) + \sum_{j=1}^{n} b_j \varphi(z_i - z_j)$$

for $i = 1, \ldots, n$ subject to the constraints:

$$\sum_{j=1}^{n} b_j \pi_k(z_j) = 0$$

for $k = 1, \ldots, m$.

where the $v_i$ are the measured data points. In this embodiment, $\hat{v}(z^*)$ is a response surface model.

In one embodiment, the surrogate model is constructed using a method other than basis functions; for example, polynomial models and support vector regression.

In one embodiment, step (i) further comprises the step of:
obtaining a plurality of measured data points for each of a plurality of characteristics of an anatomical feature of an individual; and
step (ii) further comprises the step of:
using said data points to construct a surrogate model for each of said characteristics, and using said surrogate models to obtain predicted values of said characteristics at a plurality of locations.

In one embodiment the implantable medical device is an arterial stent. The implantable medical device may be a mesh arterial stent, and the design parameter the strut width of the mesh arterial stent. The design parameter may be the drug concentration of a drug eluting stent. In one embodiment, the method further comprises the steps of numerically searching to obtain the position and the value of the maximum of the characteristic from the surrogate model and orientating the stent such that the position of the maximum of the characteristic from the surrogate model corresponds to the location on said arterial stent where the strut width is a maximum. In one embodiment, the design parameter is the longitudinal ring length. In other embodiments, the design parameter is a parameter used to define the crown shape or the link shape, such as spline control points.

In one embodiment, the characteristic is the diseased tissue thickness. In a further embodiment the characteristic is the diseased tissue thickness in an artery. In a still further embodiment, the strut width at locations on the stent that correspond, when the device is implanted, to the locations of the predicted values of the diseased tissue thickness is calculated with reference to the predicted values of the diseased tissue thickness at said locations. In another embodiment, the characteristic is the degree of calcification of the diseased tissue. In a further embodiment, the characteristic is the degree of calcification of the diseased tissue in an artery. Further examples of the characteristic include the volume of the diseased tissue, the morphology of the disease, scarring, the curvature of the vessel, the size of the host location (for example, the aortic root) or the joint geometry.

According to another aspect of the present invention, there is provided a non-transitory computer program product stored on a computer-readable medium comprising instructions operative to cause a processor to execute a method of design or selecting an implantable medical device according to the present invention.

According to another aspect of the present invention, there is provided a method of manufacturing an implantable medical device, comprising the method of designing an implantable medical device according to the present invention, and further comprising the step of manufacturing an implantable medical device according to the design parameter.

According to another aspect of the present invention, there is provided an implantable medical device, manufactured according to the method of the present invention.

According to another aspect of the present invention, there is provided a method of selecting an implantable medical device from a range of existing implantable medical devices, comprising the method of selecting an implantable medical device according to the present invention.

According to another aspect of the present invention, there is provided a method of monitoring or diagnosing a disease or disorder, comprising the steps of:
  i) obtaining a plurality of measured data points of a characteristic of an anatomical feature of an individual;
  ii) using said data points to construct a surrogate model of said characteristic,
  iii) using said surrogate model to obtain a first metric of said characteristic;
  iv) comparing the first metric with a second metric of said characteristic.

In one embodiment, the surrogate model is constructed by interpolating or regressing measured data points of the characteristic.

In one embodiment, step iv) gives an indication of the progress, or the presence or absence of, the disease or disorder.

In one embodiment, step i) can be carried out by analysing an image, or other data, obtained from the patient.

In one embodiment, the measured data points obtained in step i) are obtained at a first time $t_1$, and the method further comprises the step of obtaining the second metric, which comprises the steps of:
- a) obtaining a plurality of measured data points of the characteristic of the anatomical feature of the individual at a second time $t_2$;
- b) using said data points obtained at time $t_2$ to construct a second surrogate model of said characteristic, and
- c) using said second surrogate model to obtain the second metric of said characteristic;

wherein step iv) comprises comparing the first metric and the second metric in order to determine the progress of a disease or disorder.

In one embodiment, the second surrogate model is constructed by interpolating or regressing measured data points of the characteristic.

The time $t_2$ is later than the time $t_1$. In one embodiment, the time $t_2$ is between 18 and 24 months later than the time $t_1$.

In one embodiment, the method further comprises the step of obtaining a plurality of metrics, from measured data points obtained at a plurality of times, $t_2$, $t_3$ and so on.

In one embodiment, the second metric is a standard metric used to indicate the presence, or the absence, of a disease or disorder. The standard metric may be a metric derived from multiple individuals, for example multiple healthy individuals.

In one embodiment, the method further comprises the step of obtaining the second metric, which comprises the steps of:
- a) obtaining a plurality of measured data points of the characteristic of the anatomical feature of a second individual;
- b) using said data points to construct a second surrogate model of said characteristic,
- c) using said second surrogate model to obtain the second metric of said characteristic.

In one embodiment, the second surrogate model is constructed by interpolating or regressing measured data points of the characteristic.

In one embodiment, the second individual is a healthy individual.

The metric is a standard for measuring or evaluating the extent of the disease or disorder. The metric may be a parameter or a statistic or an image, for example.

In one embodiment, the metric is an image generated from the surrogate model. In one embodiment, the metric is the maximum predicted value of the characteristic obtained from the surrogate model. In one embodiment, the metric is the global average value of the predicted value of the characteristic obtained from the surrogate model. In one embodiment, the metric is a summation of root mean square differences of the predicted values of the characteristic obtained from the surrogate model. In one embodiment, the metric is one or more predicted values of the characteristic obtained from the surrogate model.

In one embodiment, the disease is chronic obstructive pulmonary disease (COPD). Preferably, the characteristic is the thickness of the airway wall. More preferably, the data points are measured from CT slice images of the airways.

The surrogate model may be constructed using one of the methods described above. The measurements may be obtained using one of the methods described above.

In this specification, the term "a characteristic of an anatomical feature of an individual" is any objectively measurable criterion of an anatomical feature of an individual. In this specification, the term "a characteristic of an anatomical feature of an individual" includes a characteristic of an anatomical disease. For example, a characteristic of an anatomical feature of an individual includes a characteristic of diseased tissue on an arterial wall such as the thickness of said diseased tissue, the volume of plaque or the scarring of heart tissue.

In this specification, the term "surrogate model" is a mathematical model constructed of a physical property from a set of measured data points of the physical property which can be used to obtain predicted values of the property at chosen locations. Constructing a surrogate model may comprise interpolating or regressing measured data points of a characteristic to obtain a mathematical predictor of values of the characteristic, also known as a response surface model.

In this specification, the term "design parameter" is a physical attribute of the implantable medical device used to design the device. The design parameter may have a different value at different locations on the device. For example, the strut width of a mesh arterial stent is a design parameter. The value of the strut width of a mesh arterial stent may vary according to the location on the stent.

In this specification, the term "degree of calcification of the diseased tissue" is a measure of the volume of calcified plaque. This can be measured by assigning a value to a volume of plaque depending on the evidence of the presence of calcification. The value relates to the proportion of tissue of a prescribed volume (e.g. an annulus or a section of an annulus) for which there is evidence of the presence of calcification.

In this specification, the "curvature of the artery" at a location on the artery is inversely proportional to the radius of the circular arc that approximates the curve of the centre line of the artery at that location.

BRIEF DESCRIPTION OF THE FIGURES

FIG. 2d shows the image from FIG. 2c, on which lines of best fit have been constructed marking the inner and outer boundaries.

FIG. 2e shows a graph on which the points and lines of best fit from the inner and outer boundaries are plotted, where the horizontal axis is the azimuthal coordinate and the vertical axis is the radial coordinate.

FIG. 2f shows the original IVUS image, with the lines of best fit overlaid.

FIG. 8b shows a view of the stent from above, on which the length of the stent is indicated.

FIG. 8c shows a view of the stent from the side, on which the strut width and amplitude are indicated.

FIG. 8d shows a perspective view of the stent.

FIG. 8e shows a view of the stent from one end, through the stent, on which the strut thickness is indicated.

FIG. 18(a) shows a CT slice image of a human lung, with a region of the lung indicated by a square marker.

FIG. 18(b) shows a series of enlarged images of the region of the lung indicated in FIG. 18(a), taken in different slices.

DETAILED DESCRIPTION OF THE INVENTION

Figure 1:
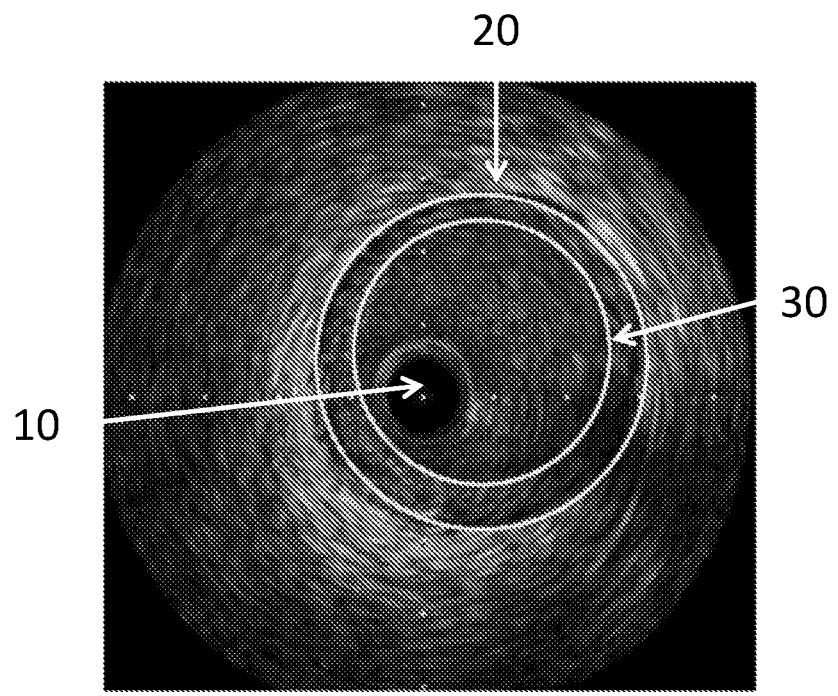
FIG. 1 shows a section through a diseased coronary artery obtained using intravascular ultrasound (IVUS).

FIG. 1 depicts a section through a diseased coronary artery obtained using intravascular ultrasound (IVUS). The dark circular disc 10 in the centre of the image is the IVUS probe. Boundaries have been superimposed on the image approximately to define the lumen (inner boundary) 30 and the outer edge of the diseased tissue (outer boundary) 20, coinciding with the media. The media is the second of three identifiable layers in the arterial wall. It is bounded by the inner and outer elastic lamina and appears as a black ring on the IVUS image. It normally defines the outer edge of the plaque. The boundaries in this case are elliptical; however they can be irregularly shaped. The outer boundary is drawn to define the outer edge of the diseased tissue. The distance between the boundaries defines the thickness of the diseased tissue.

IVUS is performed using a catheter with an ultrasound probe which is inserted into the blood vessel. IVUS images are obtained during a pull-back starting distally to the disease. The probe is initially positioned at a point which is located further along the blood vessel from the insertion point than the diseased section of the vessel. The probe is then pulled back at a constant speed, through the diseased section of the blood vessel. For example, the probe can be pulled back at a speed of 0.5 mm/sec, using a mechanical device in order to ensure that the speed remains constant. Ultrasound images are collected as the probe is pulled back. This results in a series of images, each image showing a section through the artery.

The probe generates images at a constant rate, resulting in a certain number of images per second. For example, the first image may be taken at the initial position of the probe. The probe is then pulled backwards at a rate of 0.5 mm/sec, so that the next image produced corresponds to a section of the artery that is a certain distance from the starting position. If images are generated at a rate of 30 images per second for example, then the next image shows a section of the artery at a position 0.5/30 mm from the starting position of the probe. The location of the image (x) is defined relative to the vessel centre line, in other words, x is an arc length on the centreline. The location along the artery relative to the starting position of the probe can therefore be determined for each section from the pull-back speed of the probe and the number of images captured per second.

The IVUS image in FIG. 1 shows the blood vessel wall including the diseased tissue on the inner wall. The blood is shown as a speckled region within the lumen. The inner and outer boundaries of the diseased tissue can be identified from the image. Ellipses have been added to the image in FIG. 1, identifying the inner and outer boundaries of the diseased tissue more clearly. The boundaries can be drawn onto the images by eye. Alternatively, an automated image processing method is used.

FIGS. 2a to 2f show the stages involved in a method of obtaining measurements of the diseased tissue thickness from an IVUS image showing a section of an artery that is used in accordance with one embodiment. The method involves constructing the diseased tissue boundaries by generating a polynomial representation of each boundary and then extracting the diseased tissue thickness.

Figure 2A:
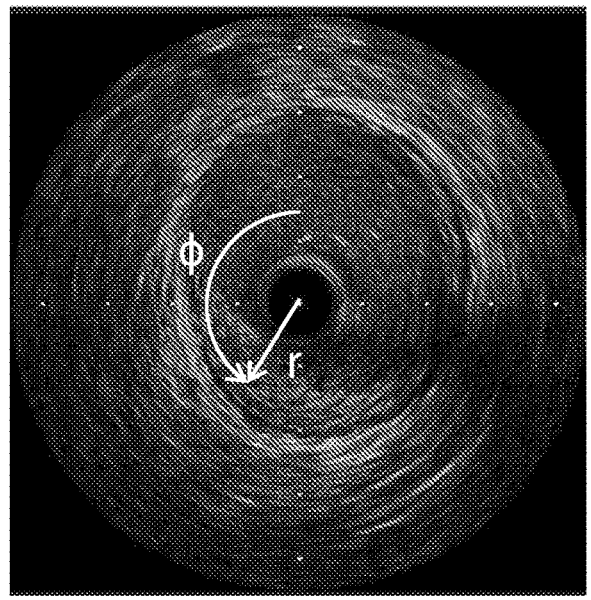
FIG. 2a shows an IVUS image of a section of a coronary artery with eccentric disease.

FIG. 2a shows an IVUS image of a section of an eccentrically diseased artery. The location of each pixel on the image is defined by an angular azimuthal coordinate, which is labelled φ on the image and a radial coordinate labelled r. The angular coordinate is measured anticlockwise from the line drawn vertically upwards from the centre of the lumen. The radial coordinate is the distance of the pixel from the central point of the probe.

The first step in the method is to transform the original IVUS image shown in FIG. 2a to a rectangular pixel grid.

Figure 2B:
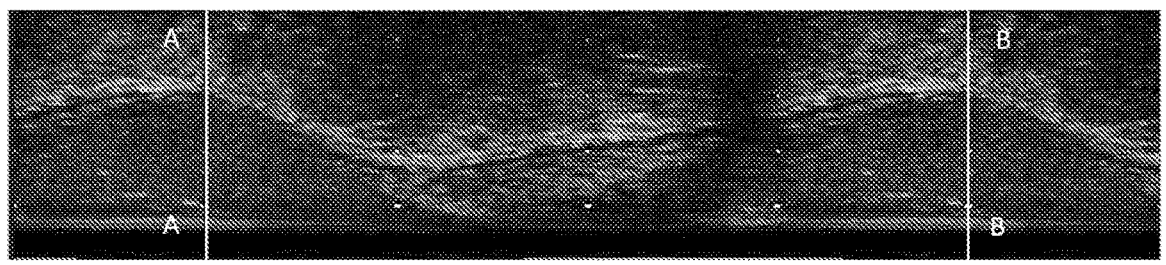
FIG. 2b shows an unwrapped pixel image obtained from the IVUS image.

FIG. 2b shows the unwrapped pixel image of the IVUS image showing a section of an artery in FIG. 2a. The complete image is contained between the lines AA and BB. The unwrapped image is obtained by transforming the polar coordinate location of each pixel in the original image to a location on the rectangular grid, where the location of each pixel in the horizontal direction corresponds to the angular coordinate and the location in the vertical direction corresponds to the radial coordinate.

A copied section that comprises a quarter of the image from one end is added to the other end of the image, and a copied section that comprises a quarter of the image from the other end is added to the first end. This aids in the construction of the inner and outer boundaries.

Figure 2C:
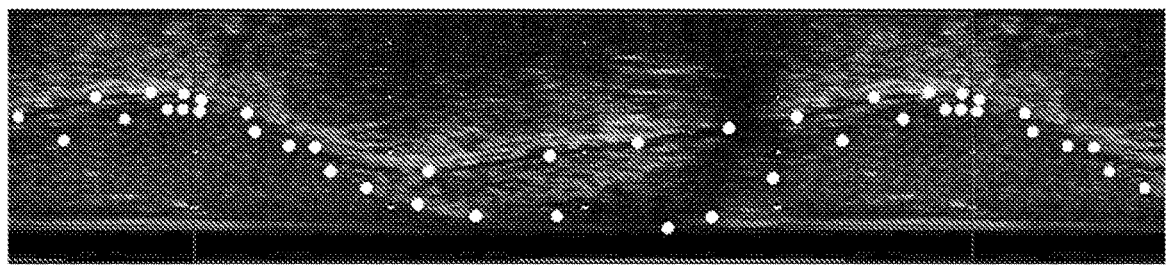
FIG. 2c shows the image from FIG. 2b, on which points are selected marking the inner and outer boundaries.

The next stage of the method involves defining points on the image corresponding to locations on the border which define the outer edge of the diseased tissue, and locations on the border which define the lumen. FIG. 2c shows the image from FIG. 2b, where discrete points have been selected for both borders. The uppermost points in the figure are those on the border between the outer edge of the diseased tissue and the outer lining of the blood vessel. The lowermost points are those on the border that defines the lumen. These points can be defined using automated methods, for example, by finding locations on the image where a step change in shading occurs. There are a number of such methods that could be used. These methods depend on the quality of the underlying image. The automated point selection can be corrected by eye if necessary. Alternatively, the points can be manually selected by eye, without the use of an automated method. Manual selection can be used when there is poor resolution in the image.

A sufficient number of points should be defined such that a line of best fit can be fitted. For the example shown in FIG. 2c, 22 points are selected for the border that defines the lumen and 18 points are selected for the border between the outer edge of the diseased tissue and the outer lining of the blood vessel. Points are selected along the entire image between lines AA and BB, and the points are also copied as part of the copied section of the image either side of lines AA and BB.

The next stage of the method involves fitting lines of best fit to the points defined in the previous step. FIG. 2d shows the image from FIG. 2c, where lines of best fit have been fitted. One line of best fit is fitted to the points that lie on the border between the outer edge of the diseased tissue and the outer lining of the blood vessel. This line is the outer boundary, and is the uppermost line in the figure. A second line is fitted to the points that lie on the border that defines the lumen. This line is the inner boundary, and is the lowermost line in the figure.

The lines shown in this figure were fitted using polynomial regression with a sixth order polynomial. However, any line of best fit or interpolation method can be used to fit the points. For example, Kriging could be used to fit a line to the points. The lines are fitted using all of the data points between AA and BB. The points outside lines AA and BB are used to help in constructing the lines.

FIG. 2e shows a plot of the lines of best fit obtained from the image. The lines and points are plotted on axes for which the unit is pixels. The horizontal axis therefore corresponds to the angular location measured anticlockwise from the line vertically up from the centre of the probe on the original image, where one unit on the axis is a single pixel. The vertical axis corresponds to the radial location measured from the centre of the probe on the original image, where one unit on the axis is a single pixel. The uppermost line in the figure is the outer boundary. The lowermost line in the figure is the inner boundary. The diseased tissue thickness at a desired angle can now be calculated as the vertical distance between the upper and lower lines at the corresponding location on the horizontal axis. In order to calculate the diseased tissue thickness therefore, the difference between the predicted value of the line of best fit that is the outer boundary and the predicted value of the line of best fit that is the inner boundary at a particular location on the horizontal axis corresponding to the desired angular location is calculated.

FIG. 2f shows the inner and outer boundary overlaid onto the original IVUS image. This step is not necessary in order to calculate the diseased tissue thickness. In order to overlay the boundaries onto the image, the inverse transform as was performed in the initial step is performed on the image shown in FIG. 2d.

Figure 3:
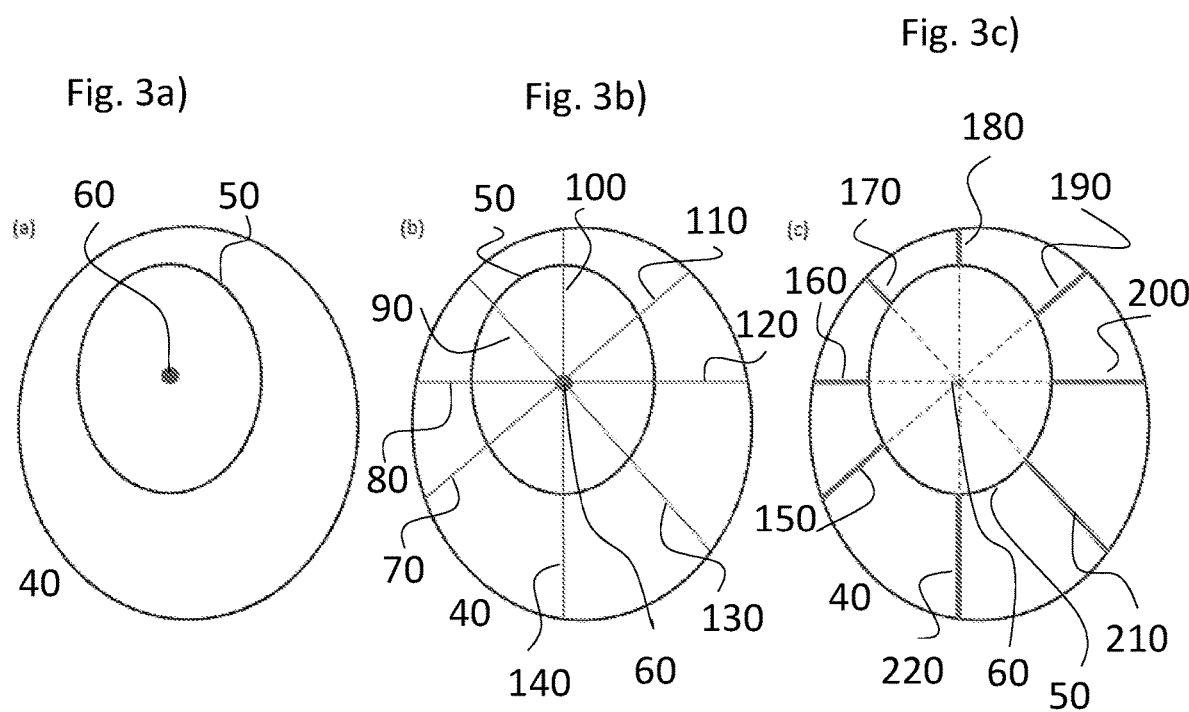
FIG. 3a shows the inner and outer disease boundaries obtained from a section through an artery, in which the centre of the lumen is defined.
FIG. 3b shows the boundaries obtained from a section through an artery, in which lines are drawn from the centre of the lumen.
FIG. 3c shows the boundaries obtained from a section through an artery, in which the distance measured along each line is highlighted.

FIGS. 3a) to c) show the stages involved in obtaining measurements of the diseased tissue thickness from an IVUS image showing a section of an artery in an alternative method that is used in accordance with an alternative embodiment. For each IVUS section, diseased tissue thickness can be generated in a three step process, shown in FIGS. 3a to 3c. The diseased tissue thickness is measured at a number of locations around the vessel for each section. Discrete locations are defined circumferentially around the vessel for which measurements of the thickness are made. Data is therefore obtained regarding the 360 degree variation of radial diseased tissue thickness for each section and this is plotted against the location along the vessel or arc length x and the angle. First, the centre of the lumen is defined. The central point of the lumen can be found using an automated image processing method. Alternatively, the central point can be found by a clinician, simply by making measurements of the image using, for example, a ruler. An automated approach can be used initially, and this can then be corrected by eye.

Lines are then drawn from the centre of the lumen, at prescribed angles (45, 90, 135, 180, 225, 270, 315 and 360 degrees, in this case) to touch the outer boundary. Finally, the distance between the inner and outer boundaries is measured along each line and the set of distances (for each IVUS section) can be plotted for the diseased tissue thickness as a function of angle and position along the vessel.

FIG. 3a shows the boundaries obtained from an IVUS image of a section of the artery. The outer ellipse 40 marks the outer border of the diseased tissue. The inner ellipse 50 corresponds to the inner border of the diseased tissue. In the first step, the centre of the lumen 60 is defined. In other words, the central point of the inner ellipse 50 is found. The central point can be found using an automated image processing method. Alternatively, the central point can be found by a clinician, simply by making measurements of the image using, for example, a ruler. An automated approach can be used initially, and this can then be corrected by eye. It is useful for vessel reconstruction to know the centre line based on the central points of all the sections. It is also useful to know the catheter line, which is the line through the centre of the probe in each section.

FIG. 3b shows the next stage of the process, in which straight lines are drawn from the centre point 60 to the outer boundaries 40. The figure shows the same outer boundary 40 and inner boundary 50 obtained from an IVUS image of a section of the artery as in FIG. 3a, with the centre of the lumen 60. Lines (70, 80, 90, 100, 110, 120, 130, 140) are drawn from the centre of the lumen 60 at prescribed angles apart (45, 90, 135, 180, 225, 270, 315 and 360 degrees in this case) to touch the outer boundary 40. These lines define the angles around the artery at which the measurements of the diseased tissue thickness are made. The location of each measurement of the thickness is defined by both the distance of the section from the starting point of the probe x, and the angle circumferentially around the section $\phi$. In other words, each measurement location has a longitudinal coordinate x and an azimuthal coordinate $\phi$.

FIG. 3c shows the final stage of the process, whereby the distance between the inner boundary 50 and outer boundary 40 is measured along each line from the previous section (70, 80, 90, 100, 110, 120, 130, 140). The figure shows the same outer boundary 40 and inner boundary 50 obtained from an IVUS image of a section of the artery as in FIG. 3a, with the centre of the lumen 60. The lines (70, 80, 90, 100, 110, 120, 130, 140) from FIG. 3b, which are drawn from the centre of the lumen 60 to the outer boundary 40, are shown on the figure. The distance between the inner boundary 50 and the outer boundary 40 along each line (70, 80, 90, 100, 110, 120, 130, 140) is measured. The measured distances (150, 160, 170, 180, 190, 200, 210, 220) of the lines between the inner boundary 50 and the outer boundary 40 are indicated by the thicker part of the line. The unmeasured parts of the lines (the part of each line within the lumen) are indicated by dashed lines.

Figure 4:
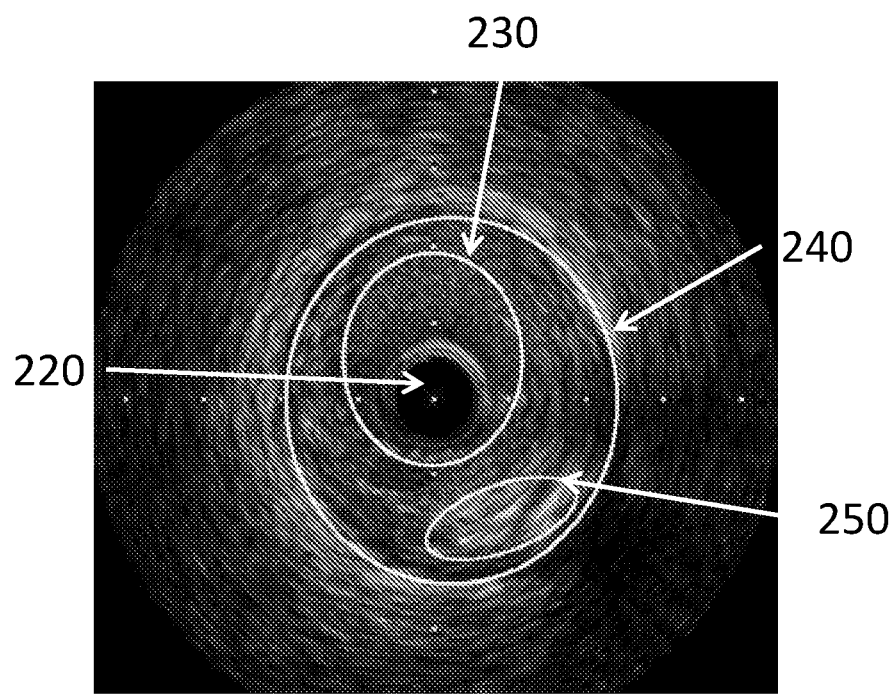
FIG. 4 shows a section through a severely diseased coronary artery obtained using IVUS.

FIG. 4 shows an IVUS image of a section of the artery taken at a different location along the artery which is in a region of more severe disease, and has a relatively tight constriction. The dark circular disk in the centre of the image 220 is the IVUS probe. Elliptical boundaries have been superimposed on the image defining the inner boundary 230 of the diseased tissue and the outer boundary 240 of the diseased tissue.

The lumen in this image is noticeably smaller than the lumen seen in the image in FIG. 1. This narrowing of the blood vessels is caused by diseased tissue, in the form of lesions or plaques that form on the inner artery walls. The diseased tissue can be formed of different types of tissue with varying rigidity. The centre of the plaques may be formed of a soft material. Areas of calcification, where calcium deposits form, have a more rigid consistency. These regions of calcification can be identified in the IVUS image as regions with relatively bright echoes with an outer dark shadow. An additional boundary 250 has been drawn on FIG. 4 to highlight a region of relatively bright echoes that is often associated with calcification. The same process of obtaining the diseased tissue thickness measurements as is shown in FIGS. 2a to 2f or FIGS. 3a to 3c is carried out using the inner boundary 230 and the outer boundary 240 obtained from the IVUS image shown in FIG. 4.

Figure 5:
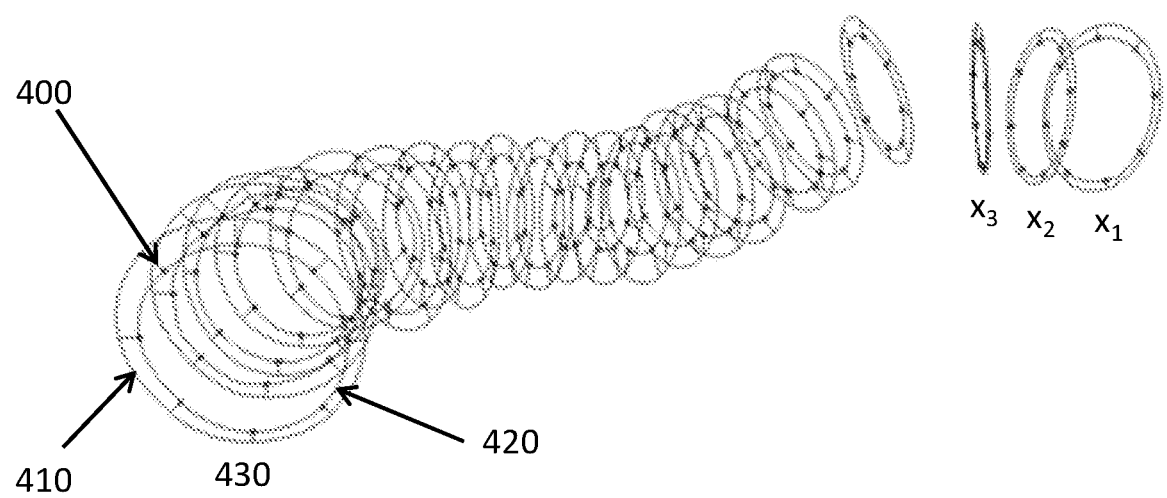
FIG. 5 shows the boundaries obtained from a series of IVUS images, aligned to correspond with their respective positions along the length of the artery.

FIG. 5 shows the boundaries and measured parts of the lines obtained from several IVUS images taken along the length of an artery. Each section has an inner and outer boundary, and between the boundaries are the sections of the lines where the measurements of the thickness are made in the process described in FIGS. 2a to 2f or FIGS. 3a to 3c. For example, for the first section 430 of the artery, the inner boundary 420, outer boundary 410 and measured parts of the lines (for example line 400) are shown. The location of each section along the blood vessel x is indicated for the first three sections as $x_1$, $x_2$ and $x_3$ respectively.

X-ray angiography data produces an image of the lumen of the blood vessel. The path of the centre of the lumen of the blood vessel can be obtained from the angiography data, for example using two orthogonal angiographic projections. A representation of the vessel centre line can therefore be obtained from X-ray angiography data. However, the line joining the centres of the lumens of each IVUS slice and the line that the IVUS probe or any catheter follows through the vessel are not necessarily the same line. The location of each IVUS image x corresponds to a location on the X-ray angiography image. The centres of the inner boundaries obtained from the IVUS image for each section of the artery are positioned to correspond approximately to the location of the vessel centre line at that point obtained from the angiography data. This means that the boundaries and measured lines from each IVUS image are positioned relative to each other such that the centres of the inner boundaries lie on the vessel centre line as obtained from the X-ray angiography data. The sections of the arteries shown in FIG. 5 are therefore positioned to be aligned with the vessel centre line. A full three-dimensional model of the vessel can be constructed by combining the stack of two-dimensional planar images with an appropriate representation of the vessel centre line obtained from X-ray angiography. Data regarding the curvature of the artery can be calculated from the data used to construct the vessel centre line.

The catheter line can be assumed to be the same as the line joining the centres of the probe in each IVUS image. The IVUS sections therefore can alternatively be positioned on the catheter line. In this case, each section is aligned such that the centre of the probe is positioned on the catheter line.

It is not required to align the images in order to obtain measurements of the diseased tissue thickness. Measurements of the diseased tissue thickness are made by measuring the distance between the inner boundary and the outer boundary. Each thickness measurement simply corresponds to a longitudinal location along the measured part of the artery x, and an azimuthal location which is an angle around the artery wall $\phi$.

Figure 6A:
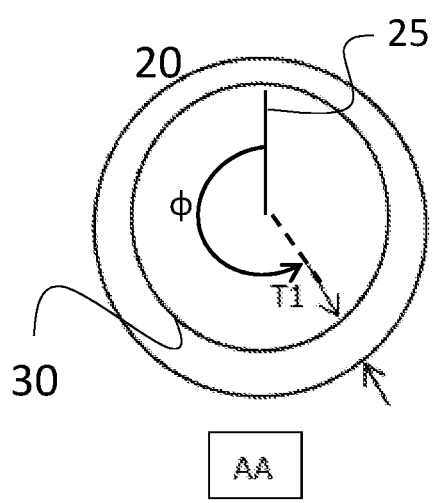
FIG. 6a shows the boundaries obtained from the IVUS image of FIG. 1, showing the position of a measurement T1.

FIG. 6a shows the boundaries obtained from the IVUS image in FIG. 1. The outer boundary 20 and the inner boundary 30 are shown. A measurement of the thickness of the diseased tissue is taken at the point T1. The location of this data point is given by the angle $\phi$ of the line, and the location x of the section along the artery. The angle $\phi$ is measured from an arbitrarily chosen line, for example, the vertical line 25 upwards from the centre of the ellipse defined by the inner boundary 30. This line defines the measurement point $\phi=0$ degrees. Measurements are taken at line at angles of 45, 90, 135, 180, 225, 270 and 315 degrees around the boundary from the line 20.

Figure 6B:
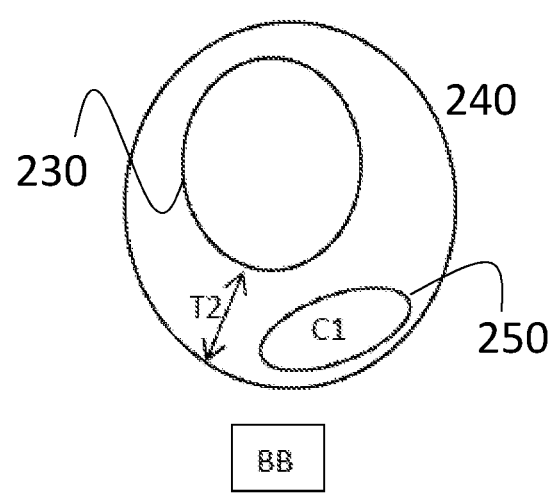
FIG. 6b shows the boundaries obtained from the IVUS image of FIG. 4, showing the position of a measurement T2.

FIG. 6b shows the boundaries obtained from the IVUS image in FIG. 4 of a section of the artery. The inner boundary 230 and the outer boundary 240 are shown. The boundary 250 highlighting the area of calcification C1 is also shown. A data point which is a measurement of the thickness of the disease tissue is taken at the point T2 for this section. The measurement of the diseased tissue thickness is the length of the part of the line from the centre point of the inner boundary 230 to the outer boundary 240, between the inner boundary 230 and the outer boundary 240. The location of this data point is given by the angle $\phi$ of the line from the vertical line upwards from the centre of the inner boundary and the location of the section along the artery x. The angle $\phi$ is therefore measured from the same reference as for the first section in FIG. 5a, i.e. the vertical upwards line from the centre of the ellipse defined by the inner boundary. This line defines the measurement point 0 degrees for all sections.

Figure 7:
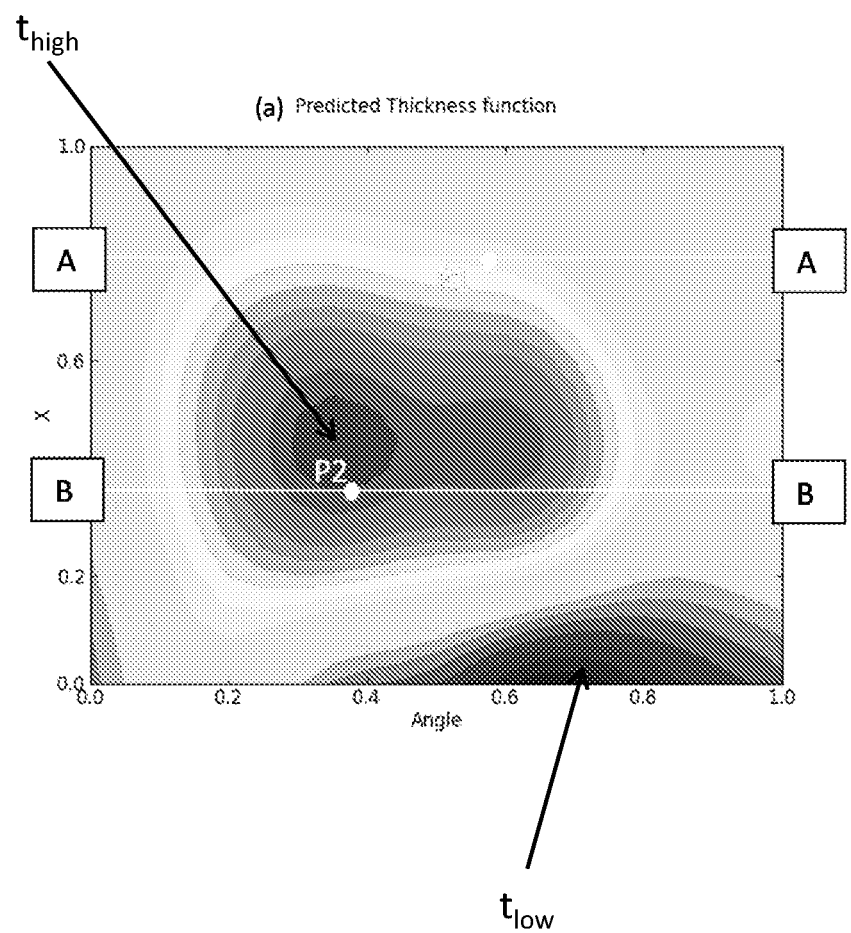
FIG. 7 shows a contour map of the predicted thickness of the diseased tissue, plotted against location along the artery on the vertical axis and the angle around the artery on the horizontal axis, generated using Kriging.

FIG. 7 shows a contour map of the diseased tissue thickness plotted against the location along the vessel or arc length (x) and the angle $\phi$. All data is non-dimensionalised with the angle $\phi$ varying between zero and 360 degrees, which corresponds to 0 to 1 on the horizontal axis of the plot. The arc length, x, is arbitrarily defined for the vessel segment such that it extends either side of the constriction a distance sufficient to extract data for device design or selection. The zero point of the arc length x is taken as an arbitrarily defined point that is distal to the diseased region. This is essentially the reference point from which the distances along the artery segment are measured. The measurements of the location along the vessel are also non-dimensionalised. The locations of the sections run from the location of the starting point, taken to be zero, to the location of the image taken furthest from the starting point, on the other side of the disease section. These locations correspond to 0 to 1 on the vertical axis. The thickness of the diseased tissue at each point is indicated by the shade of the point on the plot. The thickness is scaled on its minimum and maximum predicted values. A region of high thickness is indicated by an arrow labelled $t_{high}$. A region of low thickness is also indicated by an arrow $t_{low}$ and is in the bottom right hand corner of the plot.

The circumferential thickness variation of each section of the artery therefore corresponds to a horizontal line across the plot corresponding to the location of the section along the artery. Schematics of the boundaries obtained from the IVUS images are shown wherein the thickness variations from FIGS. 1 and 4 are defined, respectively, along lines AA and BB. Specifically, data for the thicknesses at T1 and T2 are labelled at the points P1 and P2, respectively. In other words, the thickness variation circumferentially around the artery for the section of the artery shown in the image in FIG. 1 corresponds to the line AA on the plot. The measured data for the thickness at T1 from this section is labelled at point P1. Similarly, the thickness variation around the artery for the section of the artery shown in the image in FIG. 4 corresponds to the line BB on the plot. The measured data for the thickness at T2 from this section is labelled at point P2.

This contour map is generated using the method of Kriging in this embodiment. A surrogate model of the diseased tissue thickness is constructed using the Kriging technique. Whilst other mathematical formulations are used in alternative embodiments, Kriging is a particularly useful interpolator comprising equations for expected improvement and mean square error, in addition to the predictor function itself. The predictor function used to obtain the values of the predicted diseased tissue thickness is that described in Donald R. Jones, "A Taxonomy of Global Optimization Methods Based on Response Surfaces" in Journal of Global Optimization 21, 2001, pages 345-383, which is incorporated herein by reference.

The predicted thickness function is:

$$\hat{t}(x^*) = \hat{\mu} + \sum_{i=1}^{n} b_i \varphi(x^* - x_i) \qquad \text{Eqn 1}$$

In this equation, $\hat{t}(x^*)$ is the value of the objective function (diseased tissue thickness in this case) predicted by the Kriging model at the location $$x^* = \begin{pmatrix} x^* \\ \phi^* \end{pmatrix}.$$

x* is therefore the distance along the vessel length x* and the angle around the vessel φ* of the location at which the value of the predicted diseased tissue thickness is to be obtained.

Each $x_i$ is a d-dimensional vector (where d in this case is equal to 2) which is the location of a measured data point i, that is $$x_i = \begin{pmatrix} x_i \\ \phi_i \end{pmatrix}.$$

In other words, $x_i$ is the longitudinal location along the vessel length $x_i$ and the azimuthal location which is the angle around the vessel $\phi_i$ at which a value of the diseased tissue thickness has been measured from an IVUS image. n is the number of data points used to construct the predicted diseased tissue thickness function. All selected measured points are used to construct the Kriging model. When plotting the model, a grid of points is used wherein predictions from the model are evaluated at each of these grid points. All of the selected measured data points used to construct the Kriging model are used to evaluate the predictions from the model at each grid point.

The term $\hat{\mu}$ is a constant given by:

$$\hat{\mu} = \frac{1'R^{-1}t}{1'R^{-1}1} \qquad \text{Eqn 2}$$

The term 1 is an n×1 vector of ones, $$1 = \begin{pmatrix} 1 \\ \vdots \\ 1 \end{pmatrix}.$$

The term $$t = \begin{pmatrix} t_1 \\ \vdots \\ t_n \end{pmatrix}$$

is the measured values of the diseased tissue thickness at each point $x_i$ from $x_1$ to $x_n$.

R is an n×n matrix with each element (i, j) given by the correlation function:

$$\exp\left(-\sum_{l=1}^{d} \theta_l |x_{il} - x_{jl}|^{p_l}\right) \qquad \text{Eqn 3}$$

As d=2, each element is given by:

$$\exp(-\theta_1 |x_i - x_j|^{p_1} - \theta_2 |\phi_i - \phi_j|^{p_2}) \qquad \text{Eqn 4}$$

where $(x_i, \phi_i)$ are the coordinates of a measured data point i, and $(x_j, \phi_j)$ the coordinates of a measured data point j. Where $x_i = x_j$ the correlation function is equal to 1 and as $\|x_i - x_j\| \to \infty$ the correlation function tends to zero.

The $p_l$ terms are parameters which satisfy $0 < p_l \leq 2$. Values near 2 are used to model smooth functions, and values near 0 are chosen for non-smooth functions. In one embodiment, the value of $p_l$ is set at $p_l=2$. In another embodiment, the value of $p_l$ is determined from maximising the concentrated ln-likelihood function, described below. The $\theta_l$ terms are parameters that satisfy $\theta_l \geq 0$. The estimates for the values of $\theta_l$ are obtained by numerically searching for the value of $\theta_l$ that gives the maximum of the concentrated ln-likelihood function. In one embodiment all of the values of $p_l$ and $\theta_l$ are found simultaneously in the search to maximise the concentrated ln-likelihood function. The concentrated ln-likelihood function is given by:

$$-\frac{n}{2}\ln(\hat{\sigma}^2) - \frac{1}{2}\ln(|R|) \qquad \text{Eqn 5}$$

where $$\hat{\sigma}^2 = \frac{(t-1\hat{\mu})'R^{-1}(t-1\hat{\mu})}{n} \qquad \text{Eqn 6}$$

In one embodiment, further analysis of the surrogate model is performed in order to rank the importance of the d dimensions of the measured data points.

The relative size of the $\theta_l$ values is used to identify the relative strength, or importance of each of the d dimensions, i.e. how much the response surface model, in this case the predicted thickness function $\hat{t}(x^*)$, varies with respect to variation in each dimension. In one embodiment, the values of $\theta_l$ corresponding to each dimension, d, are compared in order to gauge the relative strength of the response in the associated dimension.

The term $b_i$ is the ith element of $R^{-1}(t-1\hat{\mu})$.

The function $\varphi(x^*-x_i)$ is given by:

$$\varphi(x^* - x_i) = \exp\left(-\sum_{l=1}^{d} \theta_l |x_l^* - x_{il}|^{p_l}\right) \qquad \text{Eqn 7}$$

As d=2, the function is:

$$\varphi(x^*-x_i)=\exp(-\theta_1|x^*-x_i|^{p_1}-\theta_2|\phi^*-\phi_i|^{p_2}) \qquad \text{Eqn 8}$$

Although Kriging is the preferred method of obtaining the predicted thickness, a more general formulation of a predicted thickness function can be used, which is constructed by interpolating the measured data points using a linear combination of polynomial terms and a linear combination of radial basis function terms, given by:

$$\hat{t}(x^*) = \sum_{k=1}^{m} a_k \pi_k(x^*) + \sum_{j=1}^{n} b_j \varphi(x^* - x_j) \qquad \text{Eqn 9}$$

where again $x^*$ is the location at which the predicted diseased tissue thickness is to be obtained, $\hat{t}(x^*)$ is the predicted diseased tissue thickness at that location, and $x_j$ is the location of a measured data point. The radial basis functions are each centred around one of the measured data points. A radial basis function is a function whose value depends only on the distance from the centre, in this case the location of the measured data point.

The function $\varphi(x^*-x_j)$ is known as the basis function, and depends on the type of interpolation used. For the Kriging method, the basis function is of the form:

$$\varphi(x^* - x_j) = \exp\left(-\sum_{l=1}^{d} \theta_l |x_l^* - x_{jl}|^{p_l}\right) \qquad \text{Eqn 10}$$

However, if linear interpolation is to be used for example, then the basis function is simply given by:

$$\varphi(x^*-x_j)=\|x^*-x_j\| \qquad \text{Eqn 11}$$

If cubic interpolation is used for example, the basis function is given by:

$$\varphi(x^*-x_j)=\|x^*-x_j\|^3 \qquad \text{Eqn 11}$$

In the general case, $\pi_k(x)$ is a basis of the set of all polynomials in x of degree G. For Kriging, however, the basis function $\varphi$ is such that the polynomial term $\Sigma_{k=1}^{m} a_k \pi_k(x^*)$ is not required, and is usually a constant.

In order to determine the $a_k$ and $b_j$ terms, the following set of equations is solved:

$$t_i = \sum_{k=1}^{m} a_k \pi_k(x_i) + \sum_{j=1}^{n} b_j \varphi(x_i - x_j) \qquad \text{Eqn 13}$$

for $i = 1, \ldots, n$ subject to the additional constraint that:

$$\sum_{j=1}^{n} b_j \pi_k(x_j) = 0 \qquad \text{Eqn 14}$$

for $k = 1, \ldots, m$ where the $t_i$ are measured data points.

In an alternative embodiment, the surrogate model is constructed by methods other than basis functions, including polynomial models and support vector regression.

The predicted thickness function is used to generate the contour map in FIG. 7. A grid is defined with a specified granularity that covers the map area. The value of the predicted thickness is obtained at each intersection of the grid by evaluating the predicted thickness function at each intersection. The contour map is then drawn from the predicted values. A standard plotting package such as matplotlib can be used to produce the contour map. The contour map provides a representation of the variation of the disease.

In one embodiment, the surrogate model of the diseased tissue thickness constructed using the Kriging technique is used to design a stent such that it is optimised for the disease variation in a specific patient. A stent is a deformable tubular structure which is deployed in diseased, narrowed arteries in order to recover normal blood flow. The stent can have a mesh structure, such that it has a small diameter when crimped, and can be expanded to a larger diameter by plastic deformation. The procedure for implanting a stent is known as percutaneous coronary intervention (PCI). In the first stage of the procedure for implanting the stent, known as an angioplasty, a balloon catheter may be inserted and guided to the location in which the stent is to be implanted. The catheter is guided to the location of the diseased tissue using X-ray angiography. X-ray angiography images are viewed during the procedure, allowing the balloon to be guided into position. The balloon is then inflated, compressing the diseased tissue and widening the lumen.

This balloon catheter is then removed and a second balloon catheter, on which the stent is mounted, is inserted. If the first step of inserting the balloon catheter without the stent is omitted, then the insertion of the balloon catheter with the stent mounted is the first step in the procedure. The stent is inserted in a crimped configuration. The stent is first positioned in the artery and then the balloon is inflated, thus expanding the stent. The expanded stent provides a force outwards on the artery, compressing the diseased tissue and keeping the artery open. The balloon is then deflated and removed, and the stent is left in the vessel in the expanded configuration, in order that the blood vessel remains open.

It is important that the stent is in contact with the vessel walls. It is also important that the stent exerts enough force against the diseased tissue to compress it and force the vessel open. Where the diseased tissue is thicker, more force may be required to be exerted in order to compress the tissue and force the vessel open and maintain its patency. Similarly, for areas of high calcification, the diseased tissue is more rigid, and thus more force may be required to compress the tissue and force the artery open and maintain its patency.

Stents are often constructed of a metal mesh, and must have a relatively small diameter in the crimped form in order to be guided into the artery. A stent must be configured to expand to a larger diameter, such that it can open the blood vessel once it is positioned. Mesh stents can be made from materials other than metals, such as biodegradable polymers. Biodegradable stents open the vessel when initially positioned in the vessel, but then begin to biodegrade after a few months. The stent eventually disappears leaving a patent vessel with healthy blood flow. Drug-eluting stents also have a coating of a polymer, or another material, that contains and releases a drug to the blood vessel wall.

Figure 8A:
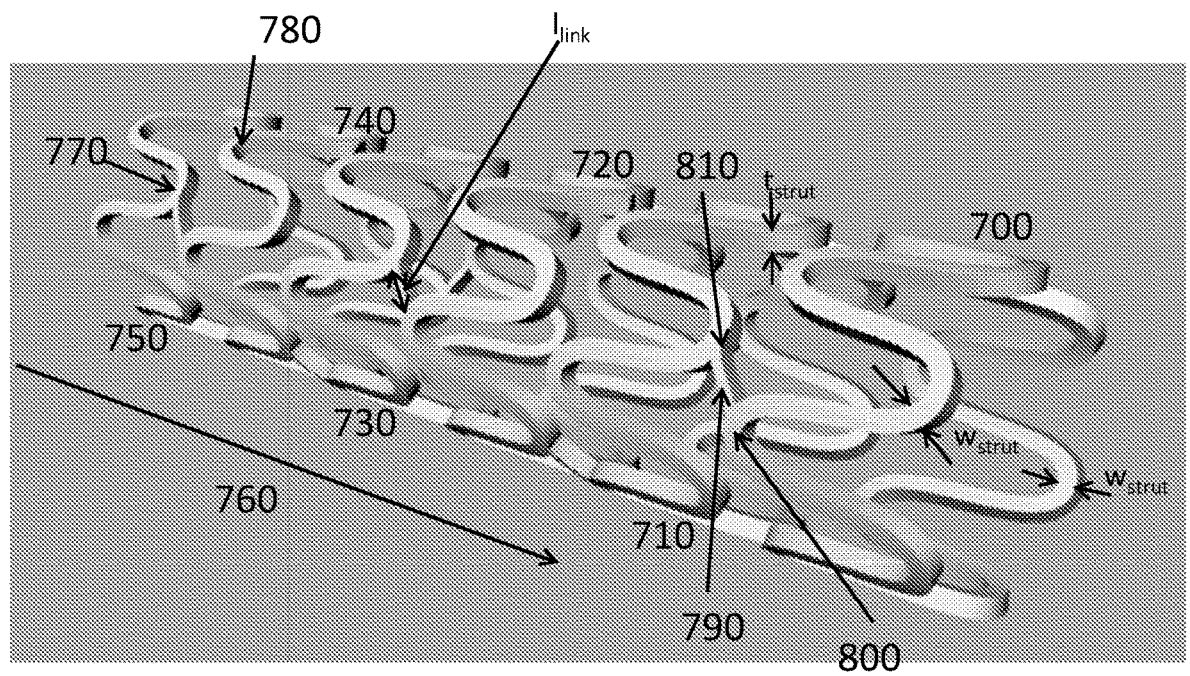
FIG. 8a shows a perspective view of a stent on which the design parameters of strut width, strut thickness and link length are indicated.

FIGS. 8a to 8c show several images of a stent design. FIG. 8a shows a stent design, that comprises a series of interconnected rings (700, 710, 720, 730, 740, 750) in a stacked configuration thus defining a tube. Adjacent rings are interconnected at predetermined intervals around the rings. Each ring has the form of a wave extending circumferentially around the tube, with the direction of the amplitude of the wave being parallel to the longitudinal axis of the tube, which is indicated by the arrow 760. In this design, the amplitude of the wave does not vary around each ring and is the same for each ring. The waves comprise a series of crowns appearing as peaks (n-shapes) 770 and troughs (u-shapes) 780. Each ring has six crowns and six troughs.

At predetermined intervals around each ring, the ring is connected to the adjacent ring by a link 790 that connects a point on the peak 800 of one ring to a point on a trough 810 of the adjacent ring. The peaks are aligned with peaks in adjacent rings. The links connect alternate peaks and troughs to the adjacent ring. In this way the rings are connected at their closest points. Every other peak of a ring is connected to a trough on the adjacent ring by means of a link. This means that every other trough on the adjacent ring is connected. The link connects from a peak to the trough that is adjacent in the clockwise direction, as seen viewed from the end of the stent that consists of the ring labelled 700. The rings and links between them form a network of struts.

There are several parameters that determine the properties of such a stent. The strut thickness is the thickness of the rings in the radial direction, which is the distance from the inner diameter of the stent to the outer diameter of the stent. The strut thickness is shown by the arrows labelled $t_{strut}$ in FIG. 8a. The strut thickness is effectively set as the thickness of the tube from which the stent is machined. The strut width is the width of the wave that forms the ring, and is shown at different locations around the ring by the two sets of arrows labelled $w_{strut}$. The strut width affects the radial strength of the stent, and also, for a drug eluting stent, the amount of drug delivered, as a wider strut has more drug coating. At the peaks and troughs of the waves, the strut width is the width in the longitudinal direction. Further parameters include the shape of the crowns, the length of the links between the rings (shown in FIG. 8a by the arrow labelled $l_{link}$), the width of these links, the shape and other dimensions of these links, the total length of the stent, and the amplitude of the wave (i.e. the distance parallel to the longitudinal axis of the tube). A stent of a differing basic design may require further parameters to be specified. Alternative designs include those in which the links are in a different configuration, and designs in which the shape of the wave differs.

FIG. 8b shows a view of the stent design from above. The length of the stent is indicated by an arrow $l_{stent}$. FIG. 8c shows a view of the stent design from the side. The strut width is indicated by an arrow $w_{strut}$. The amplitude of the wave is indicated by an arrow A. A perspective view of the stent design, similar to that shown in FIG. 8a is also shown in FIG. 8d. A view from one end looking through the stent is shown in FIG. 8e. The strut thickness is indicated by an arrow $t_{strut}$.

The stent must be designed to be strong enough that the blood vessel remains open once the balloon is removed. Re-opened diseased vessels exert a force radially inwards on the expanded stent, and the stent must be strong enough to withstand this force in order that the vessel remains open. The force exerted radially inwards on the stent may be greater where the diseased tissue is thicker. The stent is therefore required to have a higher degree of radial strength at the locations where the diseased tissue is thicker.

In order to increase the radial strength of the stent at the locations where the diseased tissue is thicker, the design parameters of the stent are varied according to predicted values of the diseased tissue thickness obtained from the surrogate model. The strut width is varied according to the predicted thickness of the diseased tissue, in order that the stent is stiffer at the points at which the thickness of the diseased tissue is greatest. The stent is stronger at the points where the strut width is largest, and therefore better able to withstand the inward radial force from the compressed diseased tissue at these points.

It is not desirable that the stent has a high strut width at all locations, as the stent is then less flexible, making it more difficult to implant into the vessel and fit the shape of the vessel. Therefore it is desirable that the stent is designed to have a small strut width at locations where the diseased tissue thickness is small, and a large strut width at the locations where the diseased tissue thickness is large. Further, variation in the strut width, and hence area of the struts also correlates to variation in the amount of drug available to be eluted into the vessel walls. A greater strut width therefore means a larger drug dosage. Therefore, increasing the strut width means a higher drug dosage and greater scaffolding.

Having constructed the map(s) of the disease, it is possible to extract data to be used to define the design or selection of a device. In this case, the design of a stent is linked to the map of diseased tissue thickness. The stent can be positioned relative to the location of maximum diseased tissue thickness, which is determined by numerically searching for the maxima of the predicted thickness function. The variation in disease along the length of an arterial segment is represented as a map which is constructed using the method of Kriging. The map can then be sampled and linked to the geometric design specification of a stent. In other words a patient-specific disease entity (such as diseased tissue thickness) is modelled, and then this information is used to design a bespoke device. Alternatively, the information can be used to guide selection of the most suitable device from a wide range of possible devices.

The stent position is determined relative to the location of maximum predicted diseased tissue thickness. The maximum predicted diseased tissue thickness is found by numerically searching for the maxima of the predicted thickness function $\hat{t}(x^*)$. The numerical searching is performed using a global search using a genetic algorithm followed by a local search. This method of searching is well known in the art. The location (in other words the coordinates x and $\phi$) of the point at which the predicted diseased tissue thickness function returns a maximum value and the maximum value itself are found using the numerical search. The minimum value of the predicted thickness function is found using the same searching method, but by searching for the minimum of the predicted thickness function.

The location for which the predicted thickness function returns a maximum value is used to determine the positioning of the stent. A location on the stent is chosen to correspond with the location of the maximum thickness. In this case, a peak in one of the middle rings of the stent (i.e. one of the rings closest to the point equidistant from either end of the stent) is selected to correspond to the location of maximum thickness. The width of the stent strut at this point therefore corresponds to the maximum width of the stent strut, $w_{max}$. The actual value of $w_{max}$ is simply assigned depending on the material of the device and other factors such as the vessel diameter. For a metallic alloy stent, the strut width varies between 90 and 120 microns. For a biodegradable stent, the strut width varies between 140 and 180 microns. The maximum width of the stent strut is selected to be a maximum at the thickest point of the disease in order that the stent has the largest radial strength and highest drug loading at this point.

Figure 9A:
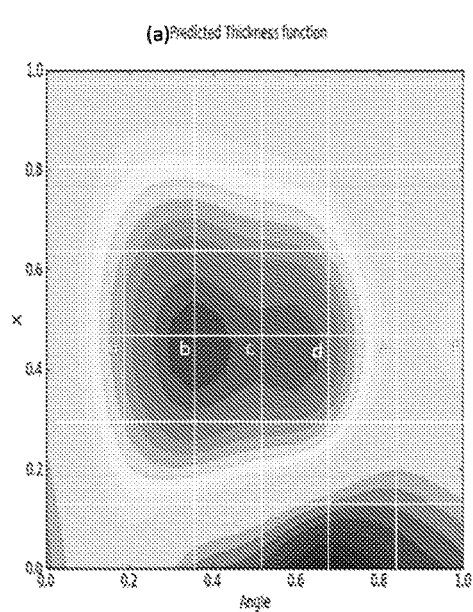
FIG. 9a shows the contour map of FIG. 7.
Figure 9B:
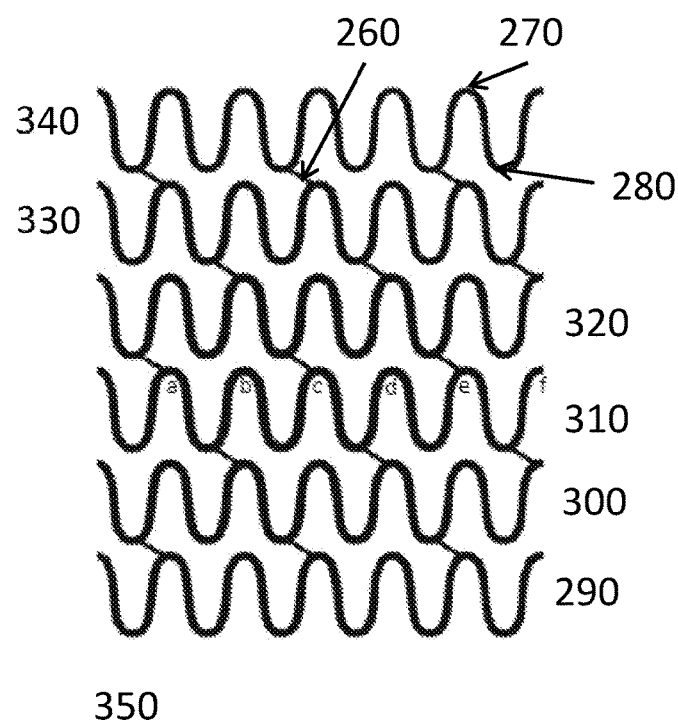
FIG. 9b shows the corresponding stent design, shown with the stent as a two dimensional net.

FIG. 9a shows the contour map of FIG. 7, and FIG. 9b shows the corresponding design of the stent. The contour map of FIG. 9a has a uniform grid overlay. The grid is defined so as to correspond to locations on the stent at which it is desired to specify inputs to the stent configuration (e.g. geometry parameters, drug concentration). At each point on the grid, data is extracted from the function and coupled to the design inputs of the stent. A 2-dimensional representation of a net of the stent is shown in FIG. 9b. Point labelled b on the grid in FIG. 9a is located in the region of peak diseased tissue thickness and corresponds to the location on the stent in FIG. 9b in which strut width is consequently prescribed its maximum value.

The stent design 350 is shown in FIG. 9b in a view in which the rings of the stent are shown as if they were flattened out. The horizontal direction corresponds to the angle circumferentially around the ring. The vertical direction corresponds to the distance along the length of the stent. The stent comprises six rings 290, 300, 310, 320, 330 and 340, which are shown in an unrolled configuration. Each flattened ring extends in a wave form with regularly spaced peaks and troughs. Each ring has six peaks and six troughs. For each ring, every other peak is connected to a trough of the adjacent ring, and every other trough is connected to a peak of the adjacent ring on the other side. The connections are such that the corresponding peak on every other ring is connected to a trough.

A point on a peak on one of the middle rings of the stent is chosen to correspond to the location for which the predicted thickness function is a maximum value. In this case, the point labelled b on the stent design is selected to correspond to the maximum predicted thickness. The stent is therefore located relative to the contour map of the predicted thickness function, by orientating the stent such that the point b on the stent design corresponds to the location of the maximum of the predicted thickness function.

The stent is designed such that the strut width at locations on the stent is determined by the predicted thickness of the disease. In this embodiment, the strut width at each of the peaks in the rings is determined by the predicted thickness of the disease at the corresponding location on the artery. Once the position of the stent is determined relative to the contour map, the locations of the crowns on the stent (for example at points a, b, c, d, e and f in the unrolled depiction of the stent in shown in FIG. 9b) are used to interpolate values from the predicted thickness function. The corresponding points on the uniform grid overlay a, b, c, d, e and f are labelled (see FIG. 9a). The points of intersection of the grid therefore correspond to the peaks on the stent design. The value of the predicted thickness function is determined at each intersection point on the grid.

For example, the points a, b, c, d, e and f in the flattened depiction of the stent in FIG. 9b correspond to the points a, b, c, d, e and f labelled on the contour map in FIG. 9a. Therefore the angle and x coordinate of the point a on the stent design corresponds to the angle and x coordinate of the point a on the contour map of the artery. The value of the predicted thickness function is determined at each of the points a, b, c, d, e and f on the contour map, and the strut width is then determined at these points. The strut width is proportional to diseased tissue thickness whereby wider struts in the vicinity of thicker disease can offer greater vessel support and/or deliver a greater concentration of drug to the vessel wall. The drug coating is dependent on the strut area and therefore the strut width. A larger strut width is coated with a larger amount of drug and therefore delivers a greater amount of drug to the patient. The strut width at a particular location on the stent is evaluated from the following equation:

$$w = w_{min} + \frac{\hat{t} - \hat{t}_{min}}{\hat{t}_{max} - \hat{t}_{min}}(w_{max} - w_{min}) \qquad \text{Eqn 15}$$

In this equation, $\hat{t}$ denotes predicted diseased tissue thickness calculated at the coordinates of the angle $\phi$ and the vessel length x of the location on the stent. $\hat{t}_{max}$ is the value of the maximum of the predicted thickness function found from the numerical search. $\hat{t}_{min}$ is the minimum of the predicted thickness function found from the numerical search. $w_{max}$ is the maximum value of the strut width, which is chosen depending on the material of the stent and other factors such as the vessel diameter. $w_{min}$ is also chosen depending on the material of the stent and other factors such as the vessel diameter as the minimum value of strut width. For a metallic alloy stent, the strut width varies between 90 and 120 microns. For a biodegradable stent, the strut width varies between 140 and 180 microns. The value of the strut width is calculated at each peak in the stent design.

Alternatively, the value of w can be evaluated at different locations on the stent. For example, the value of w can be evaluated at both the peaks and troughs of the stent design.

Figure 10:
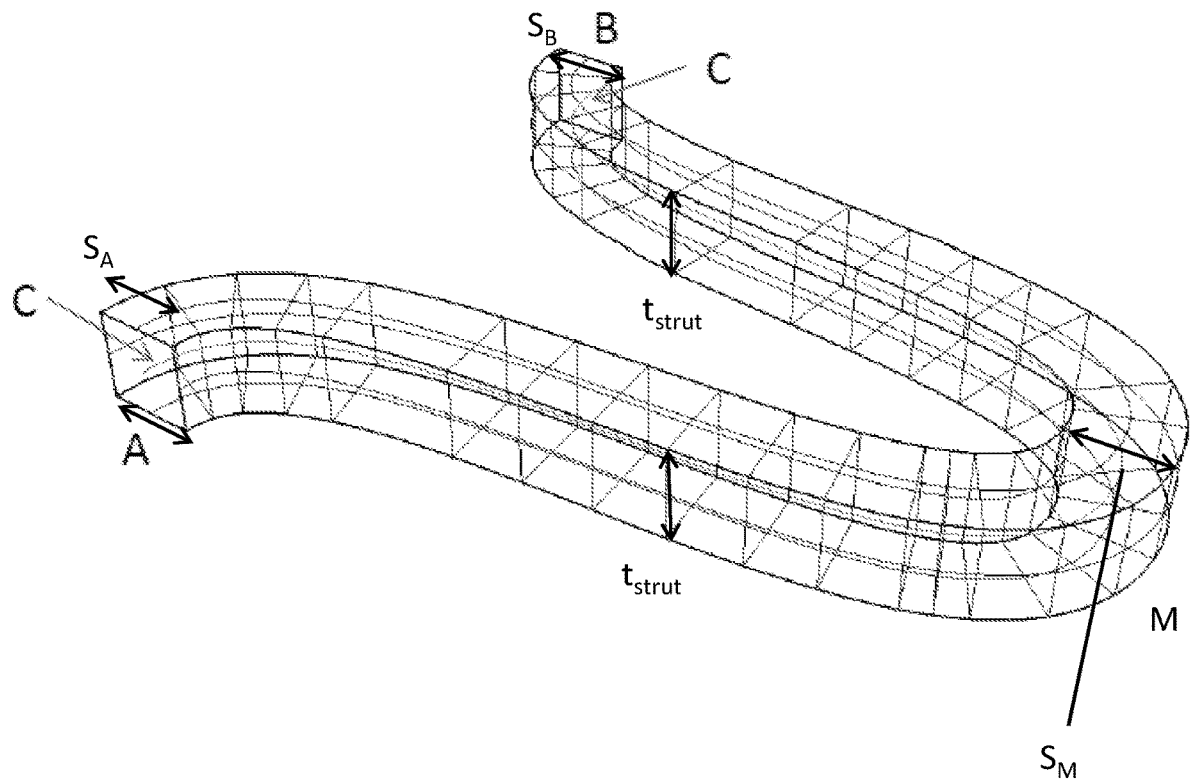
FIG. 10 shows a perspective view of a part of a stent, namely a crown.

FIG. 10 shows a section of the stent, between the locations a and b on the stent design shown in FIG. 9b. Once w is evaluated at the stent crowns, strut cross-sections are constructed (at the crowns) using these values and a fixed strut thickness. The figure shows two adjacent, rectangular cross-sections, A and B, joined by a curve, CC, between their centres and which defines the shape of the strut. The curve can be sinusoidal or a general spline with up to third order continuity or any other appropriate shape. The three dimensional struts are designed by sweeping a volume from one cross-section (A) to the other (B) along CC. This is repeated for each pair of crown cross-sections in each ring.

In order to construct the design of the section of the stent shown in FIG. 10, the predicted value of the diseased tissue thickness is calculated at the locations in the artery corresponding to the locations A and B on the stent once in position using the surrogate model constructed using the Kriging technique. The strut width is calculated from the predicted diseased tissue thickness value. The strut width at A is indicated on the figure with an arrow labelled $S_A$ and the strut width at B is indicated on the figure with an arrow labelled $S_B$.

The cross section of the stent at A is a rectangle for which the two sides which are at right angles to the direction of the amplitude of the wave are the strut thickness and the two sides that are parallel to the direction of the amplitude of the wave are the strut width $S_A$. The strut thickness is a constant value for the entire ring and therefore does not vary along the section. The strut thickness is indicated by arrows at two points on the section labelled $t_{strut}$. The strut thickness at both these points therefore is the same value, and this is the same value as at A and B. The cross section of the stent at B is a rectangle for which the two sides which are at right angles to the direction of the amplitude of the wave are the strut thickness and the two sides that are parallel to the direction of the amplitude of the wave are the strut width $S_B$.

The centre of the cross section at A and the centre of the cross section at B are joined by a line CC. The line CC is a curve. The line CC may be a sinusoidal curve for example, or may be a spline curve. The cross section of the stent runs along the curve CC such that the curve CC is always at the middle point of the cross section of the stent along the entire length of the section.

The cross section of the stent varies in size along the curve CC between point A and B. The strut thickness does not vary along the curve, however the strut width varies linearly from the value of the strut width at point A to the value of the strut width at point B. The value of the strut width at the mid-point M of the section shown (which corresponds to a trough in the wave) is therefore half way between the value of the strut width at point A and the value of the strut width at point B. The value of the strut width at the mid-point of the section shown is indicated by the arrow labelled $S_M$. Although in the design shown in FIG. 10 the strut width varies linearly between point A and point B, alternative variations in the strut width between the crowns of the stent are possible.

Figure 11:
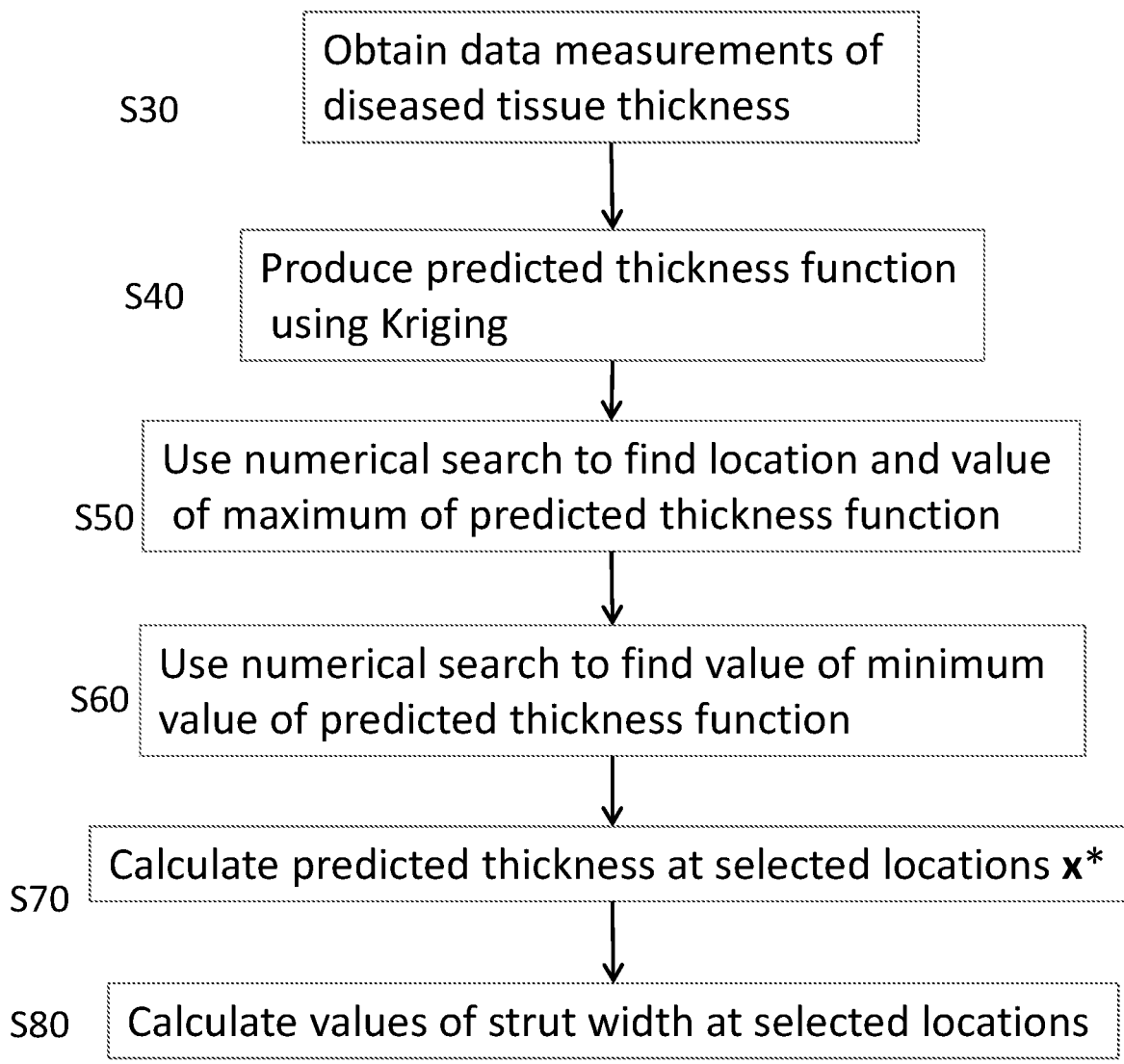
FIG. 11 is a flow chart of a method in accordance with an embodiment of the present invention, wherein a surrogate model is constructed using the method of Kriging.

FIG. 11 is a flow chart of a method in accordance with an embodiment of the present invention, wherein the surrogate model is constructed using the method of Kriging. In this method, measurements of the diseased tissue thickness taken from IVUS images of sections of the artery are used to construct a surrogate model of the diseased tissue thickness using the technique of Kriging. Predicted values of the diseased tissue thickness at chosen locations obtained from the surrogate model are then used to obtain values of the stent strut width.

In step S30 "Obtain data measurements of diseased tissue thickness" measurements of the thickness of the diseased tissue in the artery are obtained from IVUS images of sections of the artery. The location of each IVUS image along the artery determines the x coordinate of the measurements. The angle circumferentially around the artery determines the angular coordinate φ of the measurement. The next step is S40 "Produce predicted thickness function using Kriging". The predicted thickness function allows calculation of the value of the predicted thickness at any location of the modelled artery segment.

In the next step S50, "Use numerical search to find location and value of maximum of predicted thickness function" a numerical search such as a genetic search algorithm is used to determine the location of the maximum predicted thickness and the value of the maximum predicted diseased tissue thickness, and in step S60 "Use numerical search to find value of minimum value of predicted thickness function" the minimum value of the predicted diseased tissue thickness is found. The desired location of the stent is determined with reference to the position of the maximum predicted diseased tissue thickness.

In step S70, "Calculate predicted thickness at selected locations x*" the predicted thickness is calculated for specific locations on the artery that will correspond to locations on the stent when it is positioned, at which the strut width is to be determined in order to customise the design of the stent. In step S80 "Calculate values of strut width at selected locations" the values of predicted thickness are converted to values of strut width at the locations. These values are then used to design the customised stent.

It may not be possible to position the stent within the patient with sufficient rotational accuracy that the locations on the crowns of the stent correspond to the locations in the artery where the corresponding predicted values of the diseased tissue thickness were obtained. In this case, although the stent would be positioned correctly in the x direction, the rotational orientation of the stent would not be correct. The crown of the ring with the largest strut width may not then correspond to the circumferential location on the section of the artery of the greatest diseased tissue thickness. Accordingly, in some embodiments, an intermediate approach to the customised design of the stent is taken. In an embodiment, therefore, the values of the predicted diseased tissue thickness are obtained at the locations corresponding to the crowns of the stent design as before. The strut width is set to be a constant for each ring based on the mean diseased tissue thickness at the locations of the crowns of the respective ring. In other words, the mean value of the predicted diseased tissue thickness values at the crowns of one ring is found. The strut width for the entire ring is then proportional to this mean value of diseased tissue thickness, and is given by the equation:

$$w_{ring} = w_{min} + \frac{\hat{t}_{ring} - \hat{t}_{min}}{\hat{t}_{max} - \hat{t}_{min}} (w_{max} - w_{min}) \qquad \text{Eqn 16}$$

where $\hat{t}_{ring}$ is the mean value of the predicted diseased tissue thickness values obtained for each crown on the ring. Each ring on the stent may therefore have a different strut width; however, the strut width around each ring does not vary. The rotational orientation of the stent once positioned is not important, and the stent is only required to be positioned accurately in the x direction (along the artery).

In an alternative embodiment, the strut width for each ring is proportional to the maximum value in the respective set of crowns. In other words, the predicted diseased tissue thickness is obtained for the locations in the artery corresponding to the locations of the crowns of the stent for one ring. The maximum value of these predicted thickness values is used to determine the strut width for the entire ring. That is, the strut width is proportional to the maximum predicted thickness value of the predicted thickness values obtained for all the crowns on the ring. The strut width in this embodiment is constant around the ring. However the strut width may vary between the rings. The value of the strut width for a particular ring is given by $$w_{ring} = w_{min} + \frac{\hat{t}_{max_{ring}} - \hat{t}_{min}}{\hat{t}_{max} - \hat{t}_{min}}(w_{max} - w_{min}) \quad \text{Eqn 17}$$

In an alternative embodiment, the surrogate model of the diseased tissue thickness constructed using the Kriging technique described above is used to select a stent from a range of existing stents. In this embodiment, an existing range of stents, for example 10 stents, is available for a specific patient. The existing range of stents all have strut widths that are constant for the entire stent (i.e. the strut width does not vary around the ring, or between the rings). Each stent in the range has a different value of strut width.

Measurements of the thickness of the diseased tissue in the artery are obtained from IVUS images of sections of the artery and the predicted thickness function is constructed using the Kriging method as before. The predicted thickness function allows calculation of the value of the predicted thickness at any location.

In the next step, the predicted thickness is calculated at selected locations. In one embodiment, a numerical search such as a genetic search algorithm is used to determine the value of the maximum predicted diseased tissue thickness. The value of strut width from the range of strut width values of the existing stents which is most suitable for this value of predicted diseased tissue thickness is selected. The stent with this strut width is selected to be implanted into the patient. In an alternative embodiment, the predicted diseased tissue thickness is calculated at a plurality of regularly spaced locations on the diseased section of the artery. An average of these values is then determined. The value of strut width from the range of strut width values of the existing stents which is most suitable for this value of predicted diseased tissue thickness is selected, for example using a look-up table. A different look-up table is required for different vessel diameters. Other factors may influence which look-up table is used for a particular patient. An example look-up table for a vessel with a diameter of 4 mm is shown in Table 1 below.

TABLE 1

| Average predicted diseased tissue thickness (mm) | Mesh arterial stent strut width (microns) |
| --- | --- |
| 0.2 | 90 |
| 0.42 | 95 |
| 0.63 | 100 |
| 0.85 | 105 |
| 1.07 | 110 |
| 1.28 | 115 |
| 1.5 | 120 |

The stent with this strut width is selected to be implanted into the patient. One of the advantages of selecting an implantable medical device from an existing range of implantable medical devices is that the manufacturing costs are lower. Producing a large number of devices to a limited number of different designs saves in cost. The most suitable device for a specific patient is then selected from the range of manufactured devices according to the method provided in accordance with an embodiment of the present invention.

In an alternative embodiment, the existing range of stents, for example 10 stents, do not have a constant strut width for the entire stent. In this embodiment, the value of the strut width of each ring decreases linearly with increasing distance from the middle ring, such that the end rings (in both directions) have the minimum strut width and the middle ring has the maximum strut width. Each stent in the range has a different value of strut width for the middle ring.

Using the predicted thickness function obtained as described previously, a numerical search such as a genetic search algorithm is used to determine the value and location of the maximum predicted diseased tissue thickness. The value of the middle ring strut width from the range of middle ring strut width values of the existing stents which is most suitable for this value of predicted diseased tissue thickness is selected, for example using a look-up table. The stent with this strut width is selected to be implanted into the patient. The stent is located such that the middle ring corresponds to the location of maximum predicted diseased tissue thickness.

Figure 12:
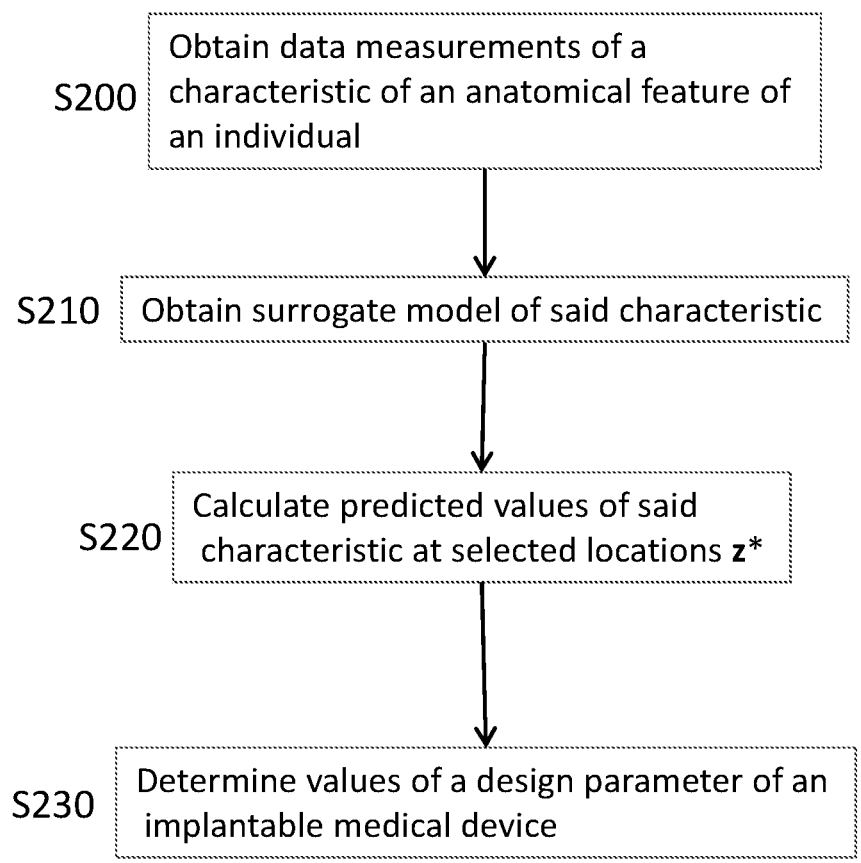
FIG. 12 is a flow chart of a method in accordance with an embodiment of the present invention.

FIG. 12 is a flow chart of a method in accordance with an embodiment of the present invention. The first step is S200 "Obtain data measurements of a characteristic of an anatomical feature of an individual". A characteristic of an anatomical feature of an individual is a characteristic of an anatomical disease in some embodiments. For example, a characteristic of an anatomical feature of an individual is a characteristic of diseased tissue on an arterial wall such as the thickness of said diseased tissue in particular embodiments. In alternative embodiments, the characteristic is the degree of calcification of said diseased tissue. In still further embodiments, the characteristic of an anatomical feature of an individual is a measurement of the curvature of the artery itself. In still further embodiments, the characteristic is the diseased tissue volume. In still further embodiments, the characteristic is the morphology of the disease. In still further embodiments, the characteristic is the degree of scarring of the tissue. Volume of diseased or scarred tissue can be measured from scans once the region of disease or scarring has been defined. The diseased or scarred volume can then be defined as a percentage of a given volume of 3D space. In still further embodiments, the characteristic is the associated anatomy, for example the size of the host location such as the aortic root or the joint geometry.

For a method of customising the design of, for example, a ureteral stent a characteristic of an anatomical feature of an individual is a measurement of the diameter of the ureter at various locations along the ureter in some embodiments. In these embodiments, the design parameters are those that define the longitudinal length of the rings, and the shapes of the crowns. The method is also applicable to the design of stents for implantation in other locations in the body, for example a urethral stent, a duodenal stent, a colonic stent or a biliary stent. For embodiments which involve the design of stents for implantation in these other locations, the characteristic may be vessel curvature. The design parameters may be those that control the flexibility of the stent, for example, the shapes of the links between the rings.

It is also to be understood that the invention is not limited to the design of stents. The present invention can be applied to the design of any implantable medical device. For the case of an implant such as a hip implant, a characteristic of an anatomical feature of an individual is a measurement of the hip socket in some embodiments. The size and shape of a patient's bones and joints are characteristics that can be used to design implants such as hip implants.

The use of Transcatheter Aortic Valve Implantation (TAVI) for replacement of stenotic aortic valves is limited by factors such as the diameter of the valve annulus, the bulk of existing leaflets, aortic diameter and degree of intrusion of the left ventricular outflow tract muscle. Bulk of existing leaflets refers to native leaflets that are not removed and present a mass of material that must be forced open and squashed between the implant and the aortic root. This provides a means for anchoring the valve in place. This anchoring may be sub-optimal in cases where unwanted paravalvular gaps persist after the procedure. The failure of the prosthesis to expand fully into the aortic root because of asymmetry of the old valve material and root can lead to paravalvular leakage. The method of the present invention can be used to customise the design of an aortic valve implant, wherein a characteristic of an anatomical feature of an individual is a measurement of the aortic size and shape or the degree of intrusion of the left ventricular outflow tract muscle, or the degree of native leaflet calcification in some embodiments. The method shown in FIG. 11 could therefore be used to customise the design parameters of the aortic valve prostheses based on predicted values of the aortic root diameter and/or the degree of intrusion of the left ventricular outflow tract muscle obtained from a surrogate model.

The next step is S210 "Produce surrogate model of said characteristic". The surrogate model can be constructed using the technique of Kriging. Alternatively, a surrogate model can be constructed using other techniques such as cubic spline interpolation, or support vector regression for example. The surrogate model allows predicted values of the characteristic to be calculated.

The next step is S220 "Calculate predicted values of said characteristic at selected locations $z^*$". The surrogate model is used to calculate predicted values of the characteristic at locations for which it is desired to obtain a value of the design parameter in order to customise the design of the device. These locations can simply be arranged in a regular grid along the device. Alternatively, it may be that there are specific locations on the device where the value of the design parameter is more critical, and therefore the predicted value of the characteristic is obtained at a location that will correspond to this location on the device once the device has been positioned.

Finally, step S230 is performed, "Determine values of a design parameter of an implantable medical device". The predicted values of the characteristic are used to calculate values for the design parameter. The values of the design parameter may be obtained by using a simple correspondence with the predicted values of the characteristic. For example, where the values of the design parameter at the location on the device which, when the device is positioned, correspond to the locations at which the predicted values of the characteristic have been obtained are related to the predicted values of the characteristic. For example, where the predicted values of the diseased tissue thickness have been obtained at locations on the artery that correspond to the crowns on the stent when the stent is positioned, the values of the strut width at the crowns on the stent are calculated with reference to the predicted values of the diseased tissue thickness at those locations.

Alternatively, where the rotational orientation of the stent cannot be controlled with accuracy, the predicted values of the diseased tissue thickness can be used to obtain the mean predicted thickness value for the location of each ring of the stent. The strut width for this ring is then directly proportional to the mean diseased tissue thickness value. Alternatively, the strut width for a ring can be taken to be directly proportional to the largest predicted thickness value for all the crowns in the ring. The correspondence between the predicted values of the characteristic and the design parameters for the device is not limited to a simple linear correspondence.

Figure 13:
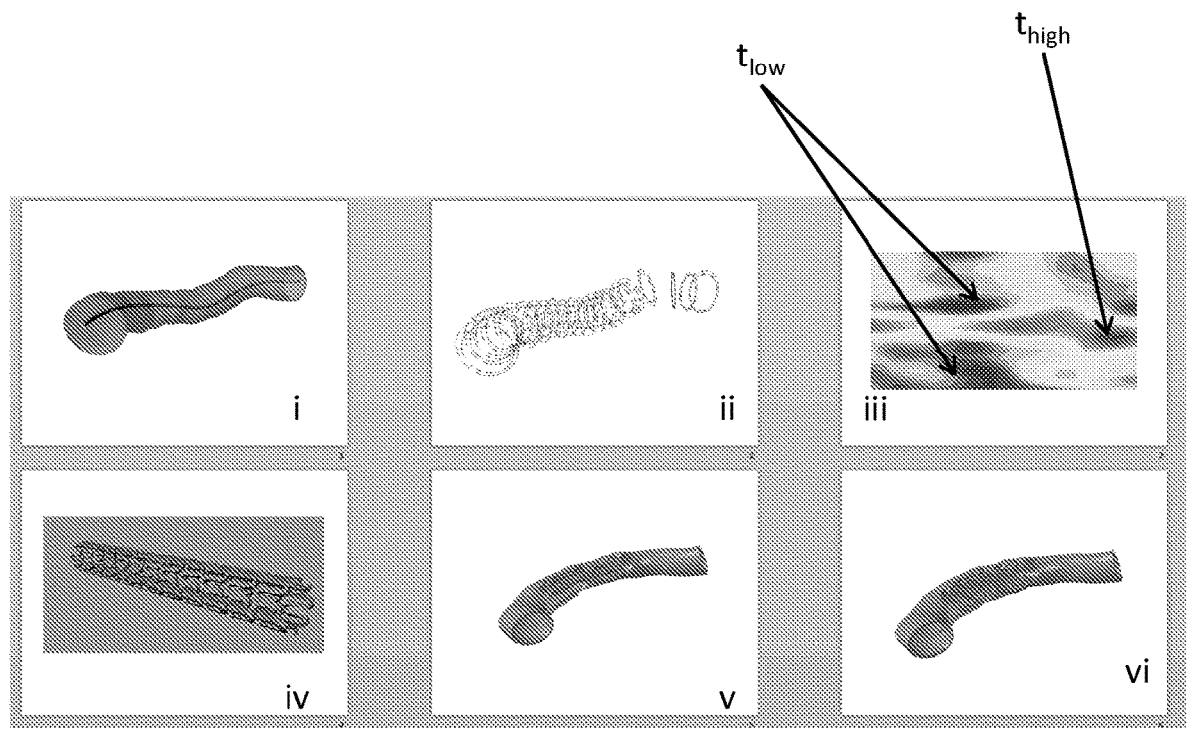
FIG. 13 shows a series of images, i to vi, showing the stages of the stent design and implantation, where i) shows a coronary artery segment, ii) the sections obtained from ultrasound images, iii) shows a Kriging based map of segment disease thickness, iv) shows the design of the stent, v) shows the stent successfully positioned in the artery segment and vi) shows the stent deployed in the expanded configuration.

FIG. 13 shows a series of images, showing the stages of the stent design and implantation. The stages involve firstly the representation of the clinically obtained imaging data, wherein a mathematical model (or map) describes the variation of disease (e.g. disease thickness or volume or plaque morphology in atherosclerotic coronary arteries) and secondly the device design based on the representation in which device design parameters are setup as functions of the output from the mathematical model. The imaging information represented on the mathematical map is used to design patient specific stents of non-uniform design optimised for the measured irregularities and non-homogeneity of the patient's disease, leading to lower rates of heart attacks, death and other complications. The design is a three stage process involving data acquisition, model construction of a predictor and then linking values from the predictor to a design parameter. The data acquisition is most likely to be obtained from anatomical images of a disease, for example intravascular ultrasound (IVUS) images used in designing coronary stents. The predictor can be any suitable mathematical function or surrogate model such as Kriging.

In order to carry out the device design method, a software suite for the design of patient specific coronary stents may be used. The device design procedure can be applied to the design of a wide range of medical devices (in addition to coronary stents).

For the case of stents, stent designs are unique to each stent company, despite the fact that there has been some convergence in the topology of all designs. All of these designs could be tailored to the method of customisation of the design. Under the patient specific customisation approach, devices can be manufactured at the time of need such that shelf life is not an issue. This means that devices do not expire and are thrown away. This reduced wastage helps lower costs. The manufacturing process of constructing the stent can involve tube production and laser cutting of the tube. Alternatively, the manufacturing process can use a metal sintering process such as 3D printing. The final stage of the manufacturing process involves electro-polishing and crimping. The computer model of the stent design (which has been generated according to the method of the invention) is different to that used in the conventional manufacturing process. Further, the designing of the stent takes place after the patient specific measurements have been made. In one embodiment, the device is designed after the measurements are taken for a specific patient. The surrogate model is constructed from these measurements and the predicted values of the characteristic are determined at specific locations. The values of the design parameter at specific locations are determined from these predicated values. A computer model of the design of the stent is constructed using these parameters, and the computer model is then sent to a remote site to be manufactured. The manufacturing can involve producing a tube to the required dimensions and then cutting the tube with a laser. Alternatively, the manufacturing can involve 3D printing of the device from the computer model of the design of the stent. The device is then setup i.e. crimped on a balloon catheter and packaged before being dispatched and implanted in the patient. Conventionally on the other hand, devices are made from a common computer model, and then crimped and packaged before being sent and then stored until required for a patient in need of a stent with those dimensions.

The image i) shows a coronary artery segment specific to a patient. A predicted catheter line is indicated along the length of the vessel. In image ii) the sections obtained from ultrasound images along the length of the segment are shown. The inner and outer boundaries for each section and the thickness measurement locations are indicated on each segment. This image is identical to that shown in FIG. 5.

The image iii) shows a Kriging based map of segment thickness (obtained from the data in image ii) plotted as a function of longitudinal and azimuthal segment location. The longitudinal location x is plotted on the vertical axis and the azimuthal location $\phi$ is plotted on the horizontal axis. The thickness is indicated by the shade at each location on the map. The regions with high and low thickness are indicated by arrows. The map is obtained by constructing a surrogate model of the thickness using the technique of Kriging, and then evaluating the predicted value of the thickness at locations on a grid. The contours are then drawn using these predicted values.

The image iv) shows the design of the stent constructed using the thickness map. The design is constructed using predicted values of the thickness at locations chosen to correspond to specific locations on the stent when it is positioned in the artery. The strut width for the stent is directly proportional to the predicted thickness obtained at these locations. The image v) shows the stent in a crimped configuration positioned in the artery. Image vi) shows the stent successfully deployed in the artery segment. In image vi) the stent is in the expanded configuration, and therefore holds the vessel open.

Figure 14:
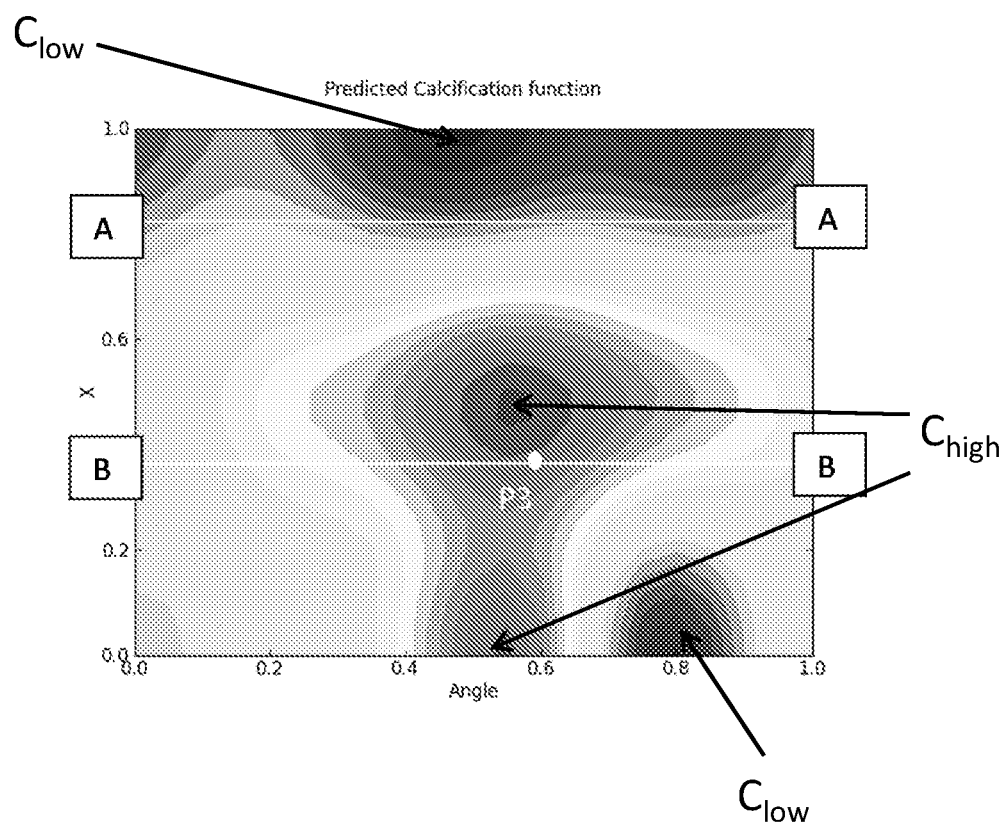
FIG. 14 shows a contour map of the degree of calcification of the diseased tissue plotted against location along the artery on the vertical axis and the angle around the artery on the horizontal axis, generated using Kriging.

FIG. 14 shows a contour map of the calcification of the disease, plotted against the location along the vessel or arc length (x) and the angle $\phi$. All data is non-dimensionalised, with the angle $\phi$ varying between zero and 360 degrees, which corresponds to 0 to 1 on the vertical axis of the plot. The arc length, x, is arbitrarily defined for the vessel segment such that it extends either side of the constriction a distance sufficient to extract data for device design or selection. The starting point of the IVUS probe is taken to be the zero point of the arc length x. This is essentially the reference point from which the distances along the artery segment are measured. The locations of the sections run from the location of the starting point, taken to be zero, to the location of the image taken furthest from the starting point. These locations correspond to 0 to 1 on the horizontal axis.

The contour map is generated using the method of Kriging. A surrogate model of the disease calcification is constructed using the Kriging technique in the same way as it was constructed for the diseased tissue thickness described above. The degree of calcification of the diseased tissue at each point corresponds to the shade of the point on the plot. The darker shaded area in the middle of the plot, near to the location of point P3, indicates where the diseased tissue has the highest degree of calcification (i.e. where the diseased tissue may need greater support to maintain vessel patency). The main areas of high calcification are labelled. The locations where the diseased tissue is less calcified are also labelled with the arrows.

The distribution of calcified plaque is likely to be more heterogeneous than the variation in diseased tissue thickness and requires a different method of measurement. Obtaining measurements that indicate the degree of calcification can involve measuring a specific volume. These measurements correspond to a percentage of the total volume that is calcified. The degree of calcification could be classified as a value of 100 where it is unequivocally identified and zero where there is no evidence for its presence; then, elsewhere, a value between 0 and 100 could be assigned based on the judgement of the clinician studying the image. The volume of tissue is assessed as a whole, and assigned a percentage value based on the percentage of the volume that is calcified. A value of 100 is assigned to a volume that is 100% calcified. Separate maps could be produced to show the distribution of the calcified, fibrous and fatty constituents of the plaque. Pre-defined volumes where there is no calcium would be assigned a value of zero percent. An automated computer method could be used to identify (and measure) calcification, the results of which the clinician could assess and manually adapt.

The variation of the calcification of the diseased tissue in a section of the artery therefore corresponds to a horizontal line across the plot corresponding to the location of the section. For example, the variation of the calcification of the diseased tissue around the artery for the section of the artery shown in the image in FIG. 1 corresponds to the line AA on the plot. Similarly, the variation in the calcification of the diseased tissue around the artery for the section of the artery shown in the image in FIG. 4 corresponds to the line BB on the plot. Point P3 labels the centre of the region, C1 shown in FIG. 6b, located in section BB.

In accordance with embodiments of the present invention, a stent for implantation in the artery is designed to be stronger where the diseased tissue is more rigid in order that the blood vessel remains open once the stent is implanted. The rigid calcified diseased tissue on the walls of the blood vessel will exert a larger force radially inwards on the expanded stent than the softer tissue, and therefore the stent must be strong enough to withstand this force in order that the vessel remains open. The stent is therefore required to have a higher degree of radial strength at the locations where the diseased tissue is more calcified. The stent requires different scaffolding properties in regions of high calcification relative to those of other morphology, for example regions where the tissue is fibrous or fatty.

In one embodiment multiple characteristics of an anatomical feature are used to determine the design parameters of the implantable medical device, wherein a number of different characteristics can be independently linked to separate design parameters or, alternatively, can be combined in cases where one or more characteristics affect a particular design parameter. A q-dimensional map of the characteristics is constructed using separate surrogate models of each characteristic, where q is the number of characteristics for which surrogate models are produced. The value of the design parameter of the device at a selected device location is calculated with reference to one or more of the q predicted characteristic values obtained from the surrogate model at the corresponding anatomical location.

For example, in one embodiment, the strut width is calculated with reference to both the predicted values of the diseased tissue thickness and the predicted values of the degree of calcification of the diseased tissue. In this embodiment, the formula for the strut width of the stent depends on both the predicted diseased tissue thickness and the predicted degree of calcification.

In another embodiment, multiple characteristics of an anatomical feature are used to determine multiple design parameters of an implantable medical device. A q-dimensional map of the characteristics is constructed using separate surrogate models of each characteristic, where q is the number of characteristics for which surrogate models are produced. The value of one design parameter of the device at a selected device location is calculated with reference to one or more of the q predicted characteristic values obtained from the surrogate models at the corresponding anatomical location. A value of a different design parameter of the device at a selected location may be calculated with reference to a different predicted characteristic value or values. Furthermore, the same predicted characteristic value or values can be used to calculate more than one design parameter in the same device design.

A further feature of the diseased artery that is used to customise design parameters of a stent in some embodiments is the curvature of the artery. The curvature of an artery can be measured from a computational model of the artery centre line constructed from orthogonal projections of the artery obtained from X-ray angiography images. The curvature at a location on the artery is inversely proportional to the radius of the circular arc that approximates the curve of the centre line of the artery at that location. Curvature can be evaluated using the Frenet-Serret formulae, relating the change of the unit tangent vector along the curve at a point, T', to the unit normal vector at that point. From this relationship, the curvature is given by the magnitude of T' (where T' is the change of the unit tangent vector). Once the centre line has been determined, a discrete set of points are defined along it. Then, at each point, numerical differentiation is used to evaluate T' and then the magnitude of this vector is evaluated to yield the curvature at the corresponding point.

In one embodiment the flexibility of the stent is coupled to the vessel curvature. The flexibility of the stent is governed by design parameters that define the shapes, positions and quantity of the links between adjacent rings. In one embodiment, the design parameters that are determined with reference to the characteristic of the curvature of the artery are independent of the other characteristics. The other characteristics, such as diseased tissue thickness and degree of calcification, are not used to determine the shapes, positions and quantities of the links. The other characteristics, such as diseased tissue thickness and degree of calcification are used to determine other design parameters such as strut width.

The accuracy of the predictor depends on many factors, including the complexity of the surrogate model, the number and locations of the measured data points and the ability of the Kriging model to predict the shape of the characteristic away from the measured data. The accuracy of the predictor determines the accuracy of the values used to obtain the device parameter at specific locations (e.g. the stent width). In some cases, it may not be known initially how much data is required in order to obtain sufficient accuracy. In these cases, the expected Improvement and/or the error function can be used to identify where to measure additional data. For the diseased tissue thickness of an artery, it may be beneficial to use a relatively small number of sections for extracting the disease thickness initially, and then use the expected improvement and/or the error function to identify other sections from which measurements are then taken.

When the surrogate model is constructed using the method of Kriging, the expected improvement and/or the error function can be used to define update points, points at which the characteristic is measured as a means of improving the accuracy of the surrogate model which is iteratively updated as new update points are defined and evaluated. In other words, characteristic values measured at update points are combined with the characteristic points already measured or calculated. The update points are locations at which further data points are measured.

In one embodiment, where the predictor function is constructed using the method of Kriging, the error function is used to find the location at which the probability of improving the predictor function by obtaining a further data point is highest. The standard error function is given by:

$$s(x) = \sqrt{\hat{\sigma}^2 \left[1 - r'R^{-1}r + \frac{(1 - r'R^{-1}r)^2}{1'R^{-1}1}\right]} \qquad \text{Eqn 18}$$

where $$r = \begin{pmatrix} \exp\left(-\sum_{l=1}^{d} \theta_l |x_l - x_{1l}|^{p_l}\right) \\ \vdots \\ \vdots \\ \exp\left(-\sum_{l=1}^{d} \theta_l |x_l - x_{nl}|^{p_l}\right) \end{pmatrix} = \qquad \text{Eqn 19}$$

$$\begin{pmatrix} \exp(-\theta_1 |x - x_1|^{p_1} - \theta_2 |\phi - \phi_1|^{p_2}) \\ \vdots \\ \vdots \\ \exp(-\theta_1 |x - x_n|^{p_1} - \theta_2 |\phi - \phi_n|^{p_2}) \end{pmatrix}$$

The location x for which the value of the standard error function is a maximum is calculated numerically. A further data point is then obtained at this location. The process is iterated, with a new data point obtained at each step, until the accuracy of the predictor function is sufficient. There are a number of methods that can be used for determining the predictive accuracy of a surrogate model including "leave one out" principles, the standardised cross validated residual (SCVR) and methods for model convergence. In one embodiment, the standard error can be monitored along with the correlation coefficient whereby the model is deemed to have converged when the standard error and the correlation coefficient have plateaued. At this stage, the iteration stops, and no further update points are obtained.

In one embodiment, where it is required to determine the location of the maximum or minimum of the predictor function, this location is used as an update location. For example, the case where the strut width of a mesh arterial stent is calculated with reference to the diseased tissue thickness and it is required to determine the location of the maximum predicted diseased tissue thickness. The location of the maximum predicted diseased tissue thickness is determined using the initial set of data points. A further data point is then obtained at this location. This process is iterated until the location and value of the maximum predicted thickness is determined with sufficient accuracy. SCVR or the mean standard error can be used to determine when the accuracy is sufficient.

In one embodiment, where the predictor function is constructed using the method of Kriging, the "expected improvement" is used to find the location at which the probability of improving the predictor function by obtaining a data point at the location is highest. The location at which the expected improvement is maximised is determined, and a data point taken at this location. These steps are iterated until the accuracy of the predictor is determined to be sufficient. There are a number of methods that can be used for determining the predictive accuracy of a surrogate model including "leave one out" principles, the standardised cross validated residual (SCVR) and methods for model convergence.

For the predicted thickness function $\hat{t}(x)$, the expected improvement is given by:

$$E(I) = s(x)[u\Phi(u) + \varphi(u)] \qquad \text{Eqn 20}$$

where $$u = \frac{f_{min} - \hat{t}(x)}{s(x)} \qquad \text{Eqn 21}$$

where $f_{min}$ is the minimum of the values of the entire set of measured data points and $s(x)$ is the standard error:

$$s(x) = \sqrt{\hat{\sigma}^2 \left[1 - r'R^{-1}r + \frac{(1 - r'R^{-1}r)^2}{1'R^{-1}1}\right]} \qquad \text{Eqn 22}$$

where $$r = \begin{pmatrix} \exp\left(-\sum_{l=1}^{d} \theta_l |x_l - x_{1l}|^{p_l}\right) \\ \vdots \\ \vdots \\ \exp\left(-\sum_{l=1}^{d} \theta_l |x_l - x_{nl}|^{p_l}\right) \end{pmatrix} = \begin{pmatrix} \exp(-\theta_1 |x - x_1|^{p_1} - \theta_2 |\phi - \phi_1|^{p_2}) \\ \vdots \\ \vdots \\ \exp(-\theta_1 |x - x_n|^{p_1} - \theta_2 |\phi - \phi_n|^{p_2}) \end{pmatrix} \qquad \text{Eqn 23}$$

$\varphi(u)$ is the probability density function $$\varphi(u) = \frac{1}{\sqrt{2\pi}} \exp\left[-\frac{u^2}{2}\right] \qquad \text{Eqn 24}$$

$\Phi(u)$ is the normal cumulative distribution function $$\Phi(u) = \frac{1}{\sqrt{2\pi}} \int_{-\infty}^{u} \exp\left[-\frac{y^2}{2}\right] dy \qquad \text{Eqn 25}$$

The normal cumulative distribution function is evaluated numerically, using the error function erf, where:

$$\Phi(u) = \frac{1}{2}\left[1 + \text{erf}\left(\frac{u}{\sqrt{2}}\right)\right] \qquad \text{Eqn 26}$$

where $$\text{erf}\left(\frac{u}{\sqrt{2}}\right) = \frac{2}{\sqrt{\pi}} \int_{0}^{\frac{u}{\sqrt{2}}} \exp[-y^2] dy \qquad \text{Eqn 27}$$

The location x at which the value of the expected improvement is a maximum is chosen to obtain the next measurement. The location at which the value of the expected improvement is a maximum is found using standard search techniques, for example using a global search followed by a local search.

In these embodiments, the surrogate model is updated by obtaining new data points at particular locations in order to improve the accuracy of the surrogate model. Where several characteristics are modelled using separate surrogate models, an update process can be performed for each surrogate model, followed by a method for positioning the device, for example using only one of the models (e.g. the diseased tissue thickness). The final steps are a method for extracting the locations x* (i.e. the locations in the patient where the characteristic is to be predicted in order to calculate the design parameters) for both predictor functions, followed by a step of predicting the characteristics and linking them to the design parameters (e.g. the strut width). The update process involves the error function and/or the expected improvement function being evaluated using the known characteristic data used to construct the Kriging model. The error function or expected improvement function is then searched to find the maximum and the update point is the location of the maximum error or expected improvement.

Figure 15:
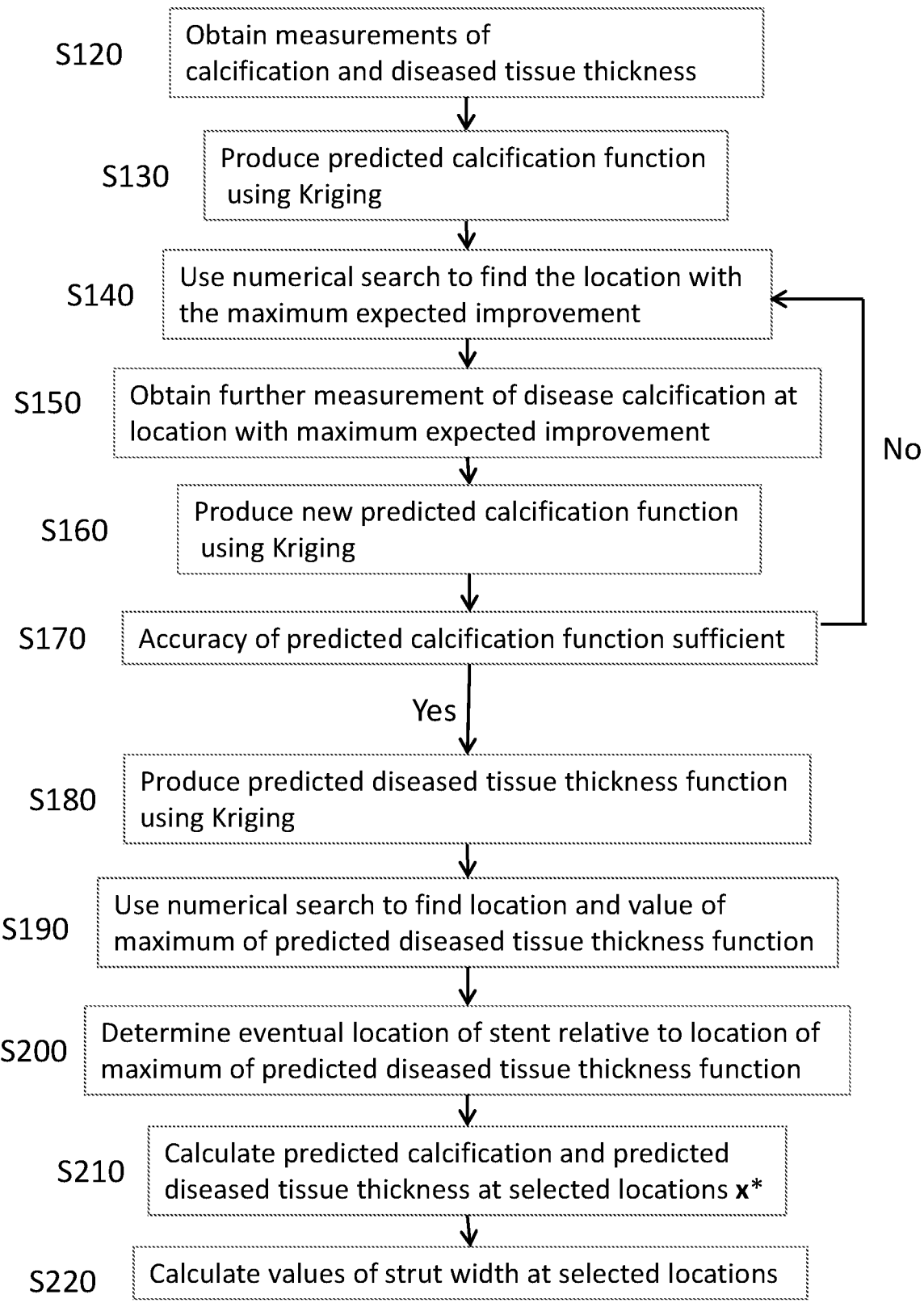
FIG. 15 is a flow chart of a method in accordance with an embodiment of the present invention, wherein the surrogate model is obtained using the method of Kriging and wherein the expected improvement is used to determine locations at which to obtain further data in order to improve the surrogate model.

FIG. 15 is a flow chart of a method in accordance with an embodiment of the present invention, wherein two surrogate models are constructed using the method of Kriging and wherein the expected improvement is used to determine locations at which to obtain further data in order to improve one of the surrogate models. In this case, the degree of calcification of the tissue and the thickness of the diseased tissue are the characteristics that are modelled in order to determine the design parameter of the device. The device in this case is an arterial stent, and the design parameter that is varied depending on the predicted values of calcification and diseased tissue thickness is the strut width. The surrogate model of the calcification is updated with further data points, the locations of which are determined using the expected improvement. The location of the device is determined based on the location of the maximum of the predicted diseased tissue thickness function. In some embodiments, it is necessary to update more than one surrogate model using the expected improvement and/or the error function.

In step 120, "Obtain measurements of calcification and diseased tissue thickness", an initial set of measurements of these characteristics of the artery are obtained. In step S130, the predicted calcification function is produced, from which it is possible to calculate the value of the predicted degree of calcification at any location.

In step S140 "Use numerical search to find the location with the maximum expected improvement", the expected improvement is used to determine the optimal location at which an additional data point which is a measurement of the degree of calcification is to be obtained in order to improve this predictor. In step S150, the data point is obtained at the location. Once the extra data point is obtained, then in step 160, the predicted calcification function is produced using the new set of data points.

In step S170, it is determined whether the accuracy of the predicted calcification function is sufficient. If it is not sufficient, then the steps from S140 to S170 are iterated. This inner loop is the update process for the calcification model and the issues discussed previously of model accuracy and convergence are important here. It is required to determine when the accuracy of the model is sufficient to stop the iteration. After the final iteration, when the accuracy of the calcification predictor is determined to be sufficient, steps S180 to S220 are performed.

In S180, "Produce predicted diseased tissue thickness function using Kriging" the surrogate model for the diseased tissue thickness is constructed. At this stage, there is already one surrogate model for the calcification, which has undergone the update process in order that more data points are added until the accuracy is sufficient. The predicted diseased tissue thickness function is a second surrogate model of the diseased tissue thickness. In step 190, "Use numerical search to find location and value of maximum of predicted diseased tissue thickness function", a numerical search such as a genetic search algorithm is used with the predicted diseased tissue thickness function in order to determine the location of the maximum predicted diseased tissue thickness and the maximum value of the predicted diseased tissue thickness function. In step S200, the desired location of the stent is determined with reference to the position of the maximum predicted diseased tissue thickness.

In step S210, "Calculate predicted calcification and predicted diseased tissue thickness at selected locations x*", the predicted calcification and diseased tissue thickness are calculated for specific locations on the artery that will correspond to locations on the stent when it is positioned at which the strut width is required to be determined. In step S220 "Calculate values of strut width at selected locations" the values of predicted calcification and diseased tissue thickness are converted to values of strut width at the locations. These values are then used to design the customised stent. The strut width can be calculated as a weighted combination of the two characteristics. A constraint that the stent strut width should be a maximum at the location of the maximum diseased tissue thickness is added when calculating the strut width. Alternatively however, the algorithm defining stent strut width as a function of diseased tissue thickness and degree of calcification could be such that the maximum stent strut width occurs at some other location. A further constraint is added to bound the stent strut width within an appropriate range as before.

Figure 16:
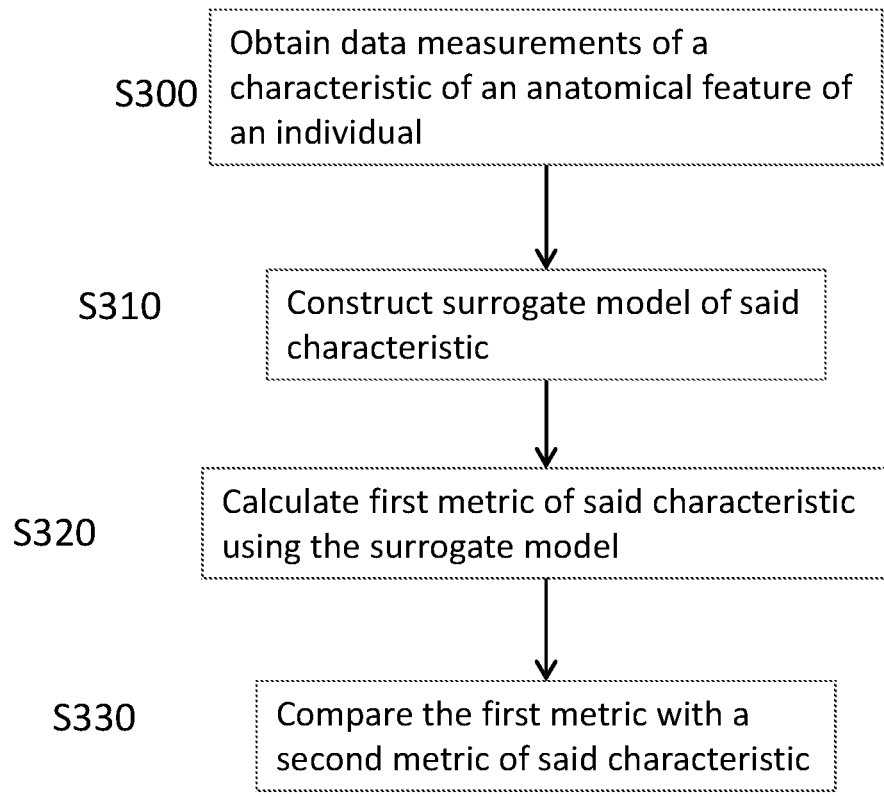
FIG. 16 shows a flow chart of a method of monitoring or diagnosing a disease or disorder in accordance with an embodiment of the present invention.

FIG. 16 shows a flow chart of a method of monitoring or diagnosing a disease or disorder in accordance with an embodiment of the present invention.

The disease may be chronic obstructive pulmonary disease (COPD) for example.

In step S300, data measurements of a characteristic of an anatomical feature of an individual are obtained. The data measurements may be obtained from an image of the anatomical feature, for example. The measurements may be of a characteristic of diseased tissue, for example. The characteristic may be the thickness of an airway wall in the lung, or a characteristic of diseased tissue on an arterial wall such as the thickness of said diseased tissue, the volume of plaque or the scarring of heart tissue.

The next step is S310 "Construct surrogate model of said characteristic".

The surrogate model may be constructed by regressing the measured data points, for example by using a least squares polynomial fit to the measured data points.

Alternatively, the surrogate model may be constructed by interpolating the measured data points using a linear combination of radial basis functions, where each radial basis function is centred around the location of a measured data point.

The surrogate model may be constructed as described in relation to Equation 9 above. In one embodiment, the surrogate model is constructed using Kriging, and as described in relation to Equation 1 above.

Step S320 is "Calculate first metric of said characteristic using the surrogate model".

In one embodiment, the first metric is a predicted value or values of the characteristic which are calculated from the surrogate model for a specific location or locations of the anatomical feature. In a further embodiment, these values are used to generate a first image, such as a contour map, from the predicted values. The first metric is an image generated from the surrogate model.

In one embodiment, the first metric is an average value of the characteristic. In one embodiment, the first metric is a maximum or minimum value of the characteristic.

In step S330, the first metric is compared with a second metric of the characteristic. The second metric may be obtained by constructing a second surrogate model of the characteristic from data measurements taken at a later point in time. Alternatively, the second metric may be obtained by constructing a second surrogate model of the characteristic from data measurements obtained from a healthy patient. Alternatively, the second metric may be a standard value or image which is known in the field to indicate the presence or absence of a disease or disorder.

In one embodiment, the first metric and the second metric are compared in order to determine progression of the disease or the disorder, or assess the impact of a treatment. Alternatively, the values may be compared in order to diagnose a disease or disorder.

Figure 17:
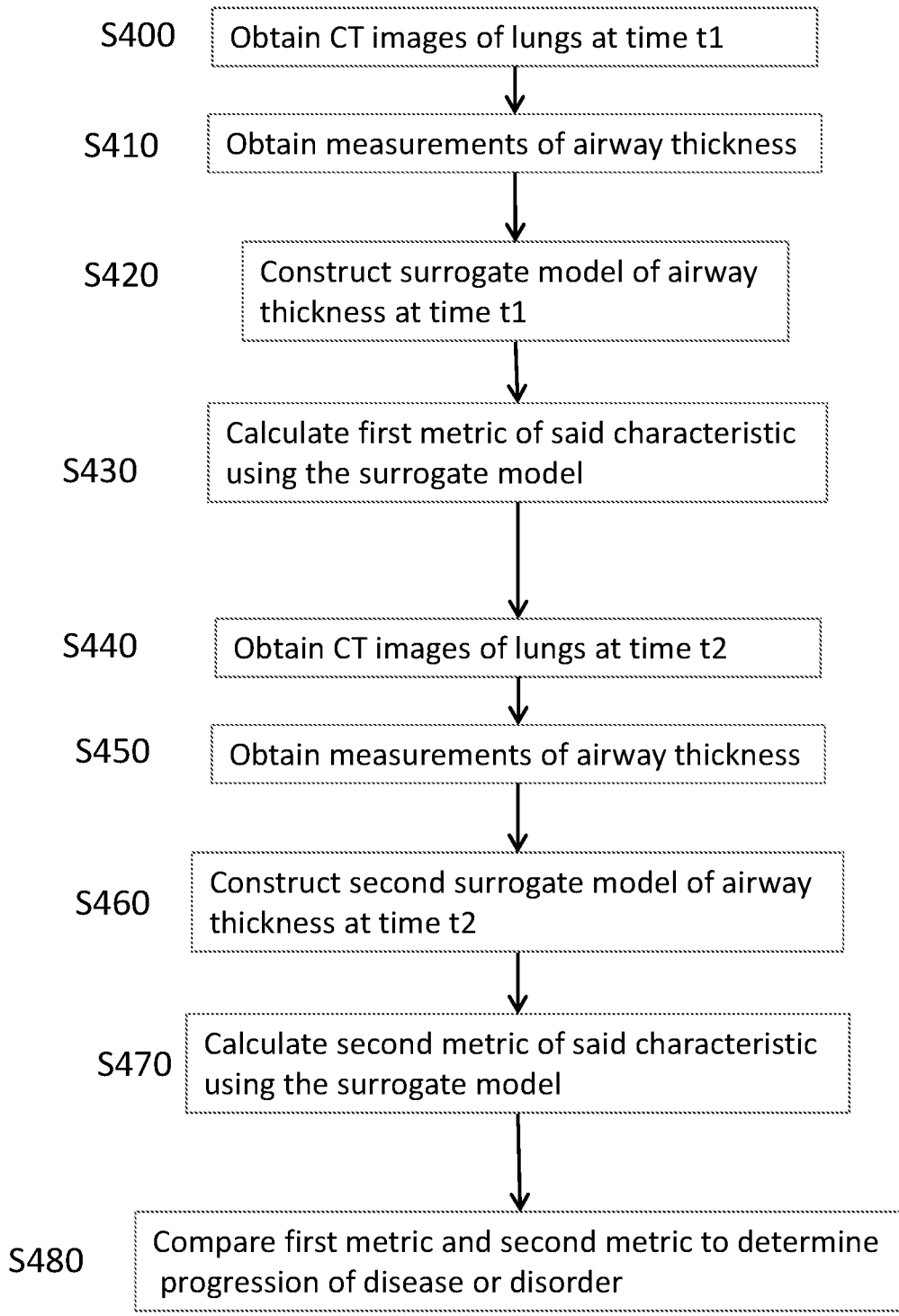
FIG. 17 shows a flow chart of a method of monitoring the progress of chronic obstructive pulmonary disease (COPD) in accordance with an embodiment of the present invention.

FIG. 17 shows a flow chart of a method of monitoring the progress of chronic obstructive pulmonary disease (COPD) in accordance with an embodiment of the present invention.

In step S400, CT images of the lungs of a patient are obtained at time t1. The CT images are a stack of parallel slices showing cuts through the intersected airways, i.e. the plane of the image intersects the airways.

FIG. 18(a) shows a CT slice image of a human lung. A region of the lung is indicated by a square marker. The light ring in the centre of the region indicated by the square defines the airway wall.

FIG. 18(b) shows a series of enlarged images of the region of the lung within the square marker, taken in different slices. In other words, the images are of the same lung, taken at different heights. The sequence of images depicts how, moving through two further slices, the airway bifurcates into separate airways in the next generation. The separate airways are shown by the smaller light rings in the second and third images.

Step S410 is "obtain measurements of airway thickness". In this step, the wall thickness of the airways is measured.

In one embodiment, the wall thickness at different radial locations around the airway for each slice image may be measured by fitting a function to points on the images corresponding to the inner and outer boundary of the airway wall. The first stage involves defining points on the image corresponding to locations on the border which define the outer boundary of the airway wall, and locations on the border which define the lumen (the inner boundary). The next stage involves fitting a function between the points defined in the previous step, giving outer and inner contours. The airway wall thickness at a desired angle can now be calculated as the distance between the contours. In order to calculate the airway wall thickness therefore, the difference between the predicted value of the function that is the outer boundary and the predicted value of the function that is the inner boundary at a particular angular location is calculated. Alternatively, the distances between the contours are directly measured from the image by counting pixels between certain points on the inner and outer contour and converting the number of pixels to a distance.

Alternatively, the airway wall thickness may be directly measured from the CT slice image, at selected radial locations around the airway. For example, the airway wall thickness may be measured using the method described in relation to FIG. 3.

Measurements of the airway wall thickness at a plurality of radial locations around the airway are obtained from each of one or more slice images, taken at locations along the airway. The location of each CT slice image along the airway determines the x coordinate of the measurements. The angle circumferentially around the airway determines the angular coordinate $\phi$ of the measurements.

The next step is S420 "Construct surrogate model of airway thickness at time t1". A surrogate model of the distribution of wall thickness at time t1 is constructed. In this step, a predicted thickness function is constructed. The predicted thickness function allows calculation of the value of the predicted thickness at any location of the modelled airway segment.

The surrogate model may be constructed by regressing the measured data points, for example by using a least squares polynomial fit to the measured data points.

Alternatively, the surrogate model may be constructed by interpolating the measured data points using a linear combination of radial basis functions, where each radial basis function corresponds to a measured data point. The surrogate model may be constructed as described in relation to Equation 9 above. In one embodiment, the surrogate model is constructed using Kriging, and as described in relation to Equation 1 above.

Step S430 is "Calculate first metric of said characteristic using the surrogate model".

In one embodiment, the first metric is a predicted value or values of the characteristic which are calculated from the surrogate model for a specific location or locations of the anatomical feature. In a further embodiment, these values are used to generate a first image, such as a contour map, from the predicted values. The first metric is an image generated from the surrogate model.

In one embodiment, a numerical search is used to find the value of the maximum of the predicted thickness obtained from the surrogate model. The maximum of the predicted thickness function may be found using a global search using a genetic algorithm followed by a local search for example.

In one embodiment, a global average wall thickness is calculated.

In step S440, further CT images of the lungs are obtained at time t2. Time t2 is later than time t1. Time t2 may be 18 to 24 months later than time t1 for example.

Step S450 is "obtain measurements of airway thickness". In this step, the wall thickness of the airways is measured from the images taken at time t2. Measurements may be obtained using the same method as used to obtain the measurements from the images taken at time t1.

The next step is S460 "Construct surrogate model of airway thickness at time t2". A surrogate model of the distribution of wall thickness at time t2 may be constructed using the same method as used in step S420 above.

Step S470 is "Calculate second metric of said characteristic using the surrogate model".

In one embodiment, the predicted thickness of the airway walls at time t2 is calculated for specific locations on the airway. The specific locations may be the same as the specific locations of the predicted thickness calculated from the first surrogate model constructed in step S420. In one embodiment, these values of predicted thickness are used to generate a second image of the airway thickness, such as a contour map.

In one embodiment, a numerical search is used to find the value of the maximum of the predicted thickness from the second surrogate model. In one embodiment, a global average wall thickness is calculated.

In step S480, the first metric and second metric are compared, in order to determine progression of the disease or the disorder, or assess treatment, or diagnose a disease or disorder.

In one embodiment, the images generated from the predicted values are compared.

In one embodiment, the maximum of the predicted thickness function at the time t1 and the maximum of the predicted thickness function at the time t2 are compared.

In one embodiment, the global average wall thickness obtained from the predicted thickness function at the time t1 and the global average wall thickness obtained from the predicted thickness function at the time t2 are compared.

In one embodiment, an increase in one of these metrics (i.e. the maximum wall thickness or global average wall thickness) indicates an adverse progression of the disease.

In one embodiment, in which the effectiveness of therapy or treatment or medication is monitored, a decrease in one of these metrics indicates an improvement in the patient's condition.

In one embodiment, a summation of wall thickness differences between the values obtained at a defined set of locations from the surrogate models of data obtained at time t1 and t2, is calculated.

In these embodiments, two or more surrogate models obtained for the same patient, each constructed from scans obtained at different points in time are used for diagnosis or for monitoring disease or disorder progression or for assessment of treatment.

Other characteristics of the airways may be modelled and used for diagnosis or for monitoring disease or disorder progression or for assessment of treatment.

In one embodiment, the CT images can be segmented to construct surrogate models of the larger airways.

In one embodiment, the images can be used to construct surrogate models of other pathophysiology, for example emphysema. In the case of emphysema, dimensions of the large, air-filled cavities are measured. These cavities appear as unwanted dark regions on a CT scan.

In one embodiment, there is provided a method of diagnosing a disease or disorder. In this embodiment, instead of steps S440 to S470, in which a second surrogate model is constructed from data taken at time t2, a second surrogate model is constructed from data taken from a healthy patient. The surrogate model constructed from data obtained at time t1 may be calibrated, such that it can be compared to the surrogate model constructed from data taken from a healthy patient.

In one embodiment, the surrogate model constructed from data obtained at time t1 is calibrated and compared to a standard surrogate model of an airway. A standard surrogate model of an airway may be constructed by obtaining measured data points at defined locations for multiple healthy individuals, averaging the measured data points for each defined location, and constructing a surrogate model from the averaged data points, for example.

The invention claimed is:
1. A method of designing or selecting an implantable heart valve, the method comprising the steps of:

i) obtaining a plurality of measured data points of a blood vessel root of a heart of an individual, the blood vessel root including obtaining a plurality of measured data points of a characteristic of diseased tissue in the blood vessel root;

ii) constructing a surrogate model of the blood vessel root by interpolating or regressing measured data points of the blood vessel root and the measured data points of the characteristic of the diseased tissue, the surrogate model including an anatomy of the blood vessel root and the characteristic of the diseased tissue;

iii) using said surrogate model to obtain predicted values of said characteristic of the diseased tissue at a plurality of locations in the blood vessel root; and iv) using the measure values and the predicted values to determine or select at least one value of a design parameter of the implantable heart valve.

2. A method according to claim 1, wherein the surrogate model is a response surface model.

3. A method according to claim 1, wherein step iv) comprises using said measured vales and said predicted values of the characteristic of the diseased tissue to determine values of the design parameter of the heart valve at locations on the heart valve that correspond, when the heart valve is implanted, to the locations of the measured valves and the predicted values of the characteristic of the diseased tissue.

4. A method according to claim 1, wherein step i) comprises obtaining the plurality of measured data points from anatomical images.

5. A method according to claim 1, wherein step ii) comprises constructing said surrogate model using the method of Kriging.

6. A method according to claim 5, further comprising the step of using an expected improvement calculation to determine further locations at which to obtain measured data points in order to improve the surrogate model.

7. A method according to claim 1, wherein step (i) further comprises the step of:

obtaining a plurality of measured data points for each of a plurality of characteristics of diseased tissue of the blood vessel root of the heart of the individual; and step (ii) further comprises the step of constructing a surrogate model of the blood vessel root by interpolating or regressing measured data points of the blood vessel root and the measured data points of the characteristics of the diseased tissue, the surrogate model including an anatomy of the blood vessel root and the plurality of characteristics of the diseased tissue; and step (iii) further comprises the step of using said surrogate model to obtain predicted values of said plurality of characteristics of the diseased tissue at a plurality of locations in the blood vessels root.

8. A method according to claim 1, wherein the characteristic of the diseased tissue is the degree of calcification of the diseased tissue in the blood vessel root.

9. A method according to claim 1, wherein step i) comprises obtaining the plurality of measured data points from a plurality of intravascular ultrasound images of sections of the blood vessel root.

10. A non-transitory computer program product stored on a computer-readable medium comprising instructions operative to cause a processor to execute a method according to claim 1.

11. A method of manufacturing an implantable heart valve, comprising the method of designing the implantable heart valve of claim 1, and further comprising the step of manufacturing the implantable heart valve according to the design parameter.

12. An implantable heart valve manufactured according to the method of claim 11.

13. A method of selecting an implantable heart valve from a range of existing implantable heart valve comprising the method of selecting the an implantable heart valve of claim 1.

14. A method according to claim 13, wherein step iv) comprises generating an image from the predicted values, wherein the at least one value of a design parameter is selected based on the image.

15. A method according to claim 1, wherein the implantable heart valve is an implantable aortic valve.

* * * * *

UNITED STATES PATENT AND TRADEMARK OFFICE
CERTIFICATE OF CORRECTION

| | | |
|---|---|---|
| PATENT NO. | : 10,642,942 B2 | Page 1 of 1 |
| APPLICATION NO. | : 15/118526 | |
| DATED | : May 5, 2020 | |
| INVENTOR(S) | : Neil W. Bressloff | |

It is certified that error appears in the above-identified patent and that said Letters Patent is hereby corrected as shown below:

On the Title Page

Item (71), in "Applicant", in Column 1, Line 1, delete "University of Southampton," and insert --Neil W. Bressloff-- therefor Signed and Sealed this
Tenth Day of November, 2020

Andrei Iancu
*Director of the United States Patent and Trademark Office*